United States Patent
Casella et al.

(10) Patent No.: US 10,457,920 B2
(45) Date of Patent: *Oct. 29, 2019

(54) STABILIZED HUMICOLA LANUGINOSA LIPASE VARIANTS IN WATER-SOLUBLE FILMS

(71) Applicants: Novozymes A/S, Bagsvaerd (DK); MONOSOL LLC, Merrrilville, IN (US)

(72) Inventors: Victor Casella, Raleigh, NC (US); Thomas Hoenger Callisen, Frederiksberg (DK); Tue Rasmussen, Copenhagen (DK); Lise Munch Mikkelsen, Roedovre (DK); Ole Simonsen, Soeborg (DK)

(73) Assignees: MONOSOL LLC, Merrillville, IN (US); Novozymes A/S, Bagsvaerd (DK)

( * ) Notice: Subject to any disclaimer, the term of this patent is extended or adjusted under 35 U.S.C. 154(b) by 427 days.

This patent is subject to a terminal disclaimer.

(21) Appl. No.: 14/891,199

(22) PCT Filed: May 14, 2014

(86) PCT No.: PCT/US2014/037999
§ 371 (c)(1),
(2) Date: Nov. 13, 2015

(87) PCT Pub. No.: WO2014/186464
PCT Pub. Date: Nov. 20, 2014

(65) Prior Publication Data
US 2016/0068787 A1    Mar. 10, 2016

(30) Foreign Application Priority Data

May 14, 2013  (EP) .................................... 13167632
May 13, 2014  (WO) ................ PCT/EP2014/059701

(51) Int. Cl.
*C12N 9/18* (2006.01)
*C12N 9/20* (2006.01)
*C11D 3/386* (2006.01)
*C11D 17/04* (2006.01)
*B65D 65/46* (2006.01)
*A61K 8/66* (2006.01)

(52) U.S. Cl.
CPC .................. *C12N 9/18* (2013.01); *A61K 8/66* (2013.01); *B65D 65/46* (2013.01); *C11D 3/38627* (2013.01); *C11D 17/042* (2013.01); *C11D 17/043* (2013.01); *C12N 9/20* (2013.01); *C12Y 301/01003* (2013.01); *C12Y 301/01* (2013.01)

(58) Field of Classification Search
None
See application file for complete search history.

(56) References Cited

U.S. PATENT DOCUMENTS

| | | | |
|---|---|---|---|
| 4,176,079 A | 11/1979 | Guerry et al. | |
| 5,892,013 A | 4/1999 | Svendsen | |
| 2009/0217464 A1 | 9/2009 | Souter | |
| 2016/0024447 A1* | 1/2016 | Simonsen | C11D 3/0042 510/393 |
| 2016/0097022 A1* | 4/2016 | Mikkelsen | C11D 3/386 510/296 |

FOREIGN PATENT DOCUMENTS

| | | |
|---|---|---|
| EP | 2395071 A1 | 12/2011 |
| WO | 2008079685 A2 | 7/2008 |
| WO | 2009083607 A1 | 7/2009 |
| WO | 2009098660 A1 | 8/2009 |
| WO | 2009/106553 A1 | 9/2009 |
| WO | 2009109500 A1 | 9/2009 |
| WO | 2010141301 A1 | 12/2010 |
| WO | 2011094470 A1 | 8/2011 |
| WO | 2013138288 A1 | 9/2013 |

* cited by examiner

*Primary Examiner* — Anand U Desai

(57) ABSTRACT

The invention relates to a lipase containing water-soluble film, and a detergent pouch formed by the water-soluble film.

16 Claims, No Drawings
Specification includes a Sequence Listing.

STABILIZED HUMICOLA LANUGINOSA LIPASE VARIANTS IN WATER-SOLUBLE FILMS

CROSS-REFERENCE TO RELATED APPLICATIONS

This application is a 35 U.S.C. 371 national application of PCT/US2014/037999 filed May 14, 2014 and published as WO02014/186464 on Nov. 20, 2014, which claims priority or the benefit under 35 U.S.C. 119 of European application no. 13167632.2 filed May 14, 2013 and EP PCT no. PCT/EP2014/059701 filed on May 13, 2014 and published as WO02014/184164 on Nov. 20, 2014.

REFERENCE TO A SEQUENCE LISTING

This application contains a Sequence Listing in computer readable form. The computer readable form is incorporated herein by reference.

FIELD OF THE INVENTION

The present invention relates to water-soluble films and detergent pouches comprising a stabilized lipase.

BACKGROUND

The use of water-soluble film packages to deliver unit dosage amounts of detergents products for e.g. laundry and automatic dish wash is well known (see e.g., WO 2009/098660 or WO 2010/141301). Both granular and liquid detergents have been on the market in this form for several years. It is also well known for decades to use enzymes in laundry detergents. More and more different types of enzymes are used in detergents, and the dosages of the enzymes is also increasing, amongst others due to the benefits coming from the enzymes and the environmental benefits of using biological actives instead of e.g. oil based chemicals like most surfactants.

A potential problem when using enzymes in detergents is the storage stability of the enzymes. Enzymes are large biological molecules that can undergo various forms of degradation. To overcome this problem numerous solutions have been suggested.

The present invention provides a solution for increasing the storage stability of lipases in water-soluble films and detergent pouch (unit dose) products by incorporating the lipase variants as disclosed in PCT/EP2014/059701.

SUMMARY

In a first aspect, the present invention provides a water-soluble film comprising a variant of a parent lipase, which variant has lipase activity, has at least 60% but less than 100% sequence identity with SEQ ID NO: 2, and comprises substitutions at positions corresponding to T231R+N233R and at least one or more (e.g., several) of D96E, D111A, D254S, G163K, P256T, G91T and G38A of SEQ ID NO: 2.

Various other aspects and embodiments are apparent from the detailed description, examples and claims.

DEFINITIONS

Lipase: The terms "lipase", "lipase enzyme", "lipolytic enzyme", "lipid esterase", "lipolytic polypeptide", and "lipolytic protein" refers to an enzyme in class EC3.1.1 as defined by Enzyme Nomenclature. It may have lipase activity (triacylglycerol lipase, EC3.1.1.3), cutinase activity (EC3.1.1.74), sterol esterase activity (EC3.1.1.13) and/or wax-ester hydrolase activity (EC3.1.1.50). For purposes of the present invention, lipase activity is determined according to the procedure described in the Examples. In one aspect, the variants of the present invention have at least 20%, e.g., at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% of the lipase activity of the polypeptide of SEQ ID NO: 2.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a polypeptide; wherein the fragment has lipase activity. In one aspect, a fragment contains at least 50%, at least 55%, at least 60%, at least 65%, at least 70%, at least 75%, at least 80%, at least 85%, at least 90%, or at least 95% but less than 100% of the number of amino acids 1 to 369 of SEQ ID NO: 2.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent lipase. Such improved properties include, but are not limited to, detergent stability, stability in detergent with protease present, protease stability, chemical stability, oxidation stability, pH stability, stability under storage conditions, and thermostability.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 269 of SEQ ID NO: 2. It is known in the art that a host cell may produce a mixture of two or more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having lipase activity. In one aspect, the mature polypeptide coding sequence is nucleotides 1 to 807 of SEQ ID NO: 1.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent lipase: The term "parent" or "parent lipase" means a lipase to which an alteration is made to produce the enzyme variants of the present invention. The parent lipase may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment).

Stability: The stability of a lipase may be expressed as the residual activity or the residual performance of said lipase during or after exposure to various test conditions such as e.g. storage in a detergent composition, at various temperatures, at various pH, in the presence of different components such as protease, chemicals, and/or oxidative substances (stress conditions). The stability of a variant lipase can be measured relative to a known activity or performance of a parent lipase, or alternatively to a known activity or performance of the variant lipase when initially added to the detergent composition optionally stored cold or frozen or relative to the variant lipase stored cold or frozen (unstressed conditions).

Subsequence: The term "subsequence" means a polynucleotide having one or more (e.g., several) nucleotides absent from the 5' and/or 3' end of a mature polypeptide coding sequence; wherein the subsequence encodes a fragment having lipase activity. In one aspect, a subsequence contains at least 50%, at least 55%, at least 60%, at least 65%, at least 70%, at least 75%, at least 80%, at least 85%, at least 90%, or at least 95% but less than 100% of the number of nucleotides 1 to 807 of SEQ ID NO: 1.

Variant: The term "variant" means a polypeptide having lipase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the lipase activity of the polypeptide of SEQ ID NO: 2.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type lipase: The term "wild-type" lipase means a lipase expressed by a naturally occurring microorganism, such as a bacterium, yeast, or filamentous fungus found in nature.

Conventions for Designation of Variants

For purposes of the present invention, the polypeptide disclosed in SEQ ID NO: 2 is used to determine the corresponding amino acid residue in another lipase. The amino acid sequence of another lipase is aligned with SEQ ID NO: 2, and based on the alignment, the amino acid position number corresponding to any amino acid residue in the polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another lipase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple Alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to water-soluble film compositions comprising a lipase variant, as disclosed in PCT/EP2014/059701, which variant comprises substitutions at positions corresponding to T231R+N233R and at least one or more (e.g., several) of the polypeptide of D96E, D111A, D254S, G163K, P256T, G91T and G38A of SEQ ID NO: 2, wherein the variant has lipase activity. The water-soluble film compositions may be used for preparing a detergent pouch, such as a detergent unit dose product.

We have found that incorporating the lipases disclosed in PCT/EP2014/059701 in a water-soluble film, provides for a water-soluble film with excellent lipase storage stability.

Therefore, the invention provides a water-soluble film and a detergent pouch comprising a lipase as disclosed in PCT/EP2014/059701, which have improved lipolytic stability. The compositions of the invention may be used in laundry and dish wash compositions and applications.

In an embodiment, the water-soluble film comprises an additional (detergent) enzyme selected from the group consisting of protease, lipase, cutinase, amylase, carbohydrase, cellulase, pectinase, mannanase, arabinase, galactanase, xylanase, DNAse, perhydrolase, and oxidase.

The storage stability of the lipase variants in the water-soluble film of the invention can be improved by including the lipase as lipase particles. This makes the lipase less prone to inactivation by detergent ingredients like bleach, surfactants, chelators etc.

Not only are the lipase variants more resistant to detergent ingredients in a detergent pouch formed by the water-soluble film, but loss of enzymatic activity during production of the water-soluble film can also be reduced. During production, the film is prepared from a hot liquid film forming composition containing the lipase variants. Both the heating step and possible proteolysis by proteases (if included) will inactivate some of the lipase variant in the hot liquid. By using lipase particles instead of dissolved lipase, the lipase becomes more resistant to inactivation.

Variants

The lipase variants (also referred to as "variants") used in the present invention, comprise substitutions at positions corresponding to T231R+N233R and at least one or more (e.g., several) of D96E, D111A, D254S, G163K, P256T, G91T and G38A of SEQ ID NO: 2, wherein the variant has lipase activity. In some aspects the variants further comprise substitutions at positions corresponding to D27R and/or N33Q of SEQ ID NO: 2.

In one aspect, the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent lipase. In another aspect, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to SEQ ID NO: 2.

In one aspect, the number of substitutions in the variants of the present invention is 1-40, e.g., 1-30, 1-20, 1-10 and 1-5, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 substitutions.

In another aspect, a variant comprises substitutions at positions corresponding to T231R+N233R and at least one or more (e.g., several) of D96E, D111A, D254S, G163K, P256T, G91T and G38A of SEQ ID NO: 2. In another aspect, a variant comprises substitutions at positions corresponding to T231R+N233R and at two positions corresponding to any of positions D96E, D111A, D254S, G163K, P256T, G91T, G38A, D27R, and N33Q of SEQ ID NO: 2. In another aspect, a variant comprises substitutions at positions corresponding to T231R+N233R and at three positions corresponding to any of positions D96E, D111A, D254S, G163K, P256T, G91T, G38A, D27R, and N33Q of SEQ ID NO: 2. In another aspect, a variant comprises substitutions at positions corresponding to T231R+N233R and at four positions corresponding to any of positions D96E, D111A, D254S, G163K, P256T, G91T, G38A, D27R, and N33Q of SEQ ID NO: 2. In another aspect, a variant comprises substitutions at positions corresponding to T231R+N233R and at five positions corresponding to any of positions D96E, D111A, D254S, G163K, P256T, G91T, G38A, D27R, and N33Q of SEQ ID NO: 2. In another aspect, a variant comprises substitutions at positions corresponding to T231R+N233R and at six positions corresponding to any of positions D96E, D111A, D254S, G163K, P256T, G91T, G38A, D27R, and N33Q of SEQ ID NO: 2. In another aspect, a variant comprises substitutions at positions corresponding to T231R+N233R and at seven positions corresponding to any of positions D96E, D111A, D254S, G163K, P256T, G91T, G38A, D27R, and N33Q of SEQ ID NO: 2. In another aspect, a variant comprises substitutions at positions corresponding to T231R+N233R and at eight positions corresponding to any of positions D96E, D111A, D254S, G163K, P256T, G91T, G38A, D27R, and N33Q of SEQ ID NO: 2. In another aspect, a variant comprises substitutions at positions corresponding to T231R+N233R and at nine positions corresponding to any of positions D96E, D111A, D254S, G163K, P256T, G91T, G38A, D27R, and N33Q of SEQ ID NO: 2.

In another aspect, the variant comprises or consists of substitutions at positions corresponding to T231R+N233R and position 96. In another aspect, the amino acid at a position corresponding to position 96 is substituted with Glu, Gly, Ser, or Val, preferably with Glu. In another aspect, the variant comprises or consists of the substitution D96E of SEQ ID NO: 2.

In another aspect, the variant comprises or consists of substitutions at positions corresponding to T231R+N233R and position 111. In another aspect, the amino acid at a position corresponding to position 111 is substituted with Ala, Gly, Ile, Leu, Met, or Val, preferably with Ala. In another aspect, the variant comprises or consists of the substitution D111A of SEQ ID NO: 2.

In another aspect, the variant comprises or consists of substitutions at positions corresponding to T231R+N233R and position 254. In another aspect, the amino acid at a position corresponding to position 254 is substituted with Ser, or Thr, preferably with Ser. In another aspect, the variant comprises or consists of the substitution D254S of SEQ ID NO: 2.

In another aspect, the variant comprises or consists of substitutions at positions corresponding to T231R+N233R and position 163. In another aspect, the amino acid at a position corresponding to position 163 is substituted with Asp, Glu, His, or Lys. In another aspect, the variant comprises or consists of the substitution G163K of SEQ ID NO: 2.

In another aspect, the variant comprises or consists of substitutions at positions corresponding to T231R+N233R and position 256. In another aspect, the amino acid at a position corresponding to position 256 is substituted with Lys, Ser, or Thr, preferably with Thr. In another aspect, the variant comprises or consists of the substitution P256T of SEQ ID NO: 2.

In another aspect, the variant comprises or consists of substitutions at positions corresponding to T231R+N233R and position 91. In another aspect, the amino acid at a position corresponding to position 91 is substituted with Ala, Asn, Gln, Glu, Ile, Leu, Ser, Thr, Trp, or Val, preferably with Thr. In another aspect, the variant comprises or consists of the substitution G91T of SEQ ID NO: 2.

In another aspect, the variant comprises or consists of substitutions at positions corresponding to T231R+N233R and position 38. In another aspect, the amino acid at a position corresponding to position 38 is substituted with Ala, Arg, Asn, Asp, Gln, Glu, Ile, Leu, Met, or Val, preferably with Ala. In another aspect, the variant comprises or consists of the substitution G38A of SEQ ID NO: 2.

In another aspect, the variant comprises or consists of substitutions at positions corresponding to T231R+N233R and position 27. In another aspect, the amino acid at a position corresponding to position 27 is substituted with Arg, His, or Lys, preferably with Arg. In another aspect, the variant comprises or consists of the substitution D27R of SEQ ID NO: 2.

In another aspect, the variant comprises or consists of substitutions at positions corresponding to T231R+N233R and position 33. In another aspect, the amino acid at a position corresponding to position 33 is substituted with Gln, Lys, Ser, or Thr, preferably with Gln. In another aspect, the variant comprises or consists of the substitution N33Q of SEQ ID NO: 2.

In another aspect, the variant comprises or consists of the substitutions at positions corresponding to T231R+N233R and one of 27+33; 27+38; 27+91; 27+96; 27+111; 27+163; 27+254; 27+256; 33+38; 33+91; 33+96; 33+111; 33+163; 33+254; 33+256; 38+91; 38+96; 38+111; 38+163; 38+254; 38+256; 91+96; 91+111; 91+163; 91+254; 91+256; 96+111; 96+163; 96+254; 96+256; 111+163; 111+254; 111+256; 163+254; 163+256; or 254+256, such as those described above.

In another aspect, the variant comprises or consists of the substitutions at positions corresponding to T231R+N233R and one of 27+33+38; 27+33+91; 27+33+96; 27+33+111; 27+33+163; 27+33+254; 27+33+256; 27+38+91; 27+38+96; 27+38+111; 27+38+163; 27+38+254; 27+38+256; 27+91+96; 27+91+111; 27+91+163; 27+91+254; 27+91+256; 27+96+111; 27+96+163; 27+96+254; 27+96+256; 27+111+163; 27+111+254; 27+111+256; 27+163+254; 27+163+256; 27+254+256; 33+38+91; 33+38+96; 33+38+111; 33+38+163; 33+38+254; 33+38+256; 33+91+96; 33+91+111; 33+91+163; 33+91+254; 33+91+256; 33+96+111; 33+96+163; 33+96+254; 33+96+256; 33+111+163; 33+111+254; 33+111+256; 33+163+254; 33+163+256; 33+254+256; 38+91+96; 38+91+111; 38+91+163; 38+91+254; 38+91+256; 38+96+111; 38+96+163; 38+96+254; 38+96+256; 38+111+163; 38+111+254; 38+111+256; 38+163+254; 38+163+256; 38+254+256; 91+96+111; 91+96+163; 91+96+254; 91+96+256; 91+111+163; 91+111+254; 91+111+256; 91+163+254; 91+163+256; 91+254+256; 96+111+163; 96+111+254; 96+111+256; 96+163+254; 96+163+256; 96+254+256; 111+163+254; 111+163+256; 111+254+256; or 163+254+256 such as those described above.

In another aspect, the variant comprises or consists of the substitutions at positions corresponding to T231R+N233R and one of 27+33+38+91; 27+33+38+96; 27+33+38+111; 27+33+38+163; 27+33+38+254; 27+33+38+256; 27+33+91+96; 27+33+91+111; 27+33+91+163; 27+33+91+254; 27+33+91+256; 27+33+96+111; 27+33+96+163; 27+33+96+254; 27+33+96+256; 27+33+111+163; 27+33+111+254; 27+33+111+256; 27+33+163+254; 27+33+163+256; 27+33+254+256; 27+38+91+96; 27+38+91+111; 27+38+91+163; 27+38+91+254; 27+38+91+256; 27+38+96+111; 27+38+96+163; 27+38+96+254; 27+38+96+256; 27+38+111+163; 27+38+111+254; 27+38+111+256; 27+38+163+254; 27+38+163+256; 27+38+254+256; 27+91+96+111; 27+91+96+163; 27+91+96+254; 27+91+96+256; 27+91+111+163; 27+91+111+254; 27+91+111+256; 27+91+163+254; 27+91+163+256; 27+91+254+256; 27+96+111+163; 27+96+111+254; 27+96+111+256; 27+96+163+254; 27+96+163+256; 27+96+254+256; 27+111+163+254; 27+111+163+256; 27+111+254+256; 27+163+254+256; 33+38+91+96; 33+38+91+111; 33+38+91+163; 33+38+91+254; 33+38+91+256; 33+38+96+111; 33+38+96+163;

33+38+96+254; 33+38+96+256; 33+38+111+163; 33+38+111+254; 33+38+111+256; 33+38+163+254; 33+38+163+256; 33+38+254+256; 33+91+96+111; 33+91+96+163; 33+91+96+254; 33+91+96+256; 33+91+111+163; 33+91+111+254; 33+91+111+256; 33+91+163+254; 33+91+163+256; 33+91+254+256; 33+96+111+163; 33+96+111+254; 33+96+111+256; 33+96+163+254; 33+96+163+256; 33+96+254+256; 33+111+163+254; 33+111+163+256; 33+111+254+256; 33+163+254+256; 38+91+96+111; 38+91+96+163; 38+91+96+254; 38+91+96+256; 38+91+111+163; 38+91+111+254; 38+91+111+256; 38+91+163+254; 38+91+163+256; 38+91+254+256; 38+96+111+163; 38+96+111+254; 38+96+111+256; 38+96+163+254; 38+96+163+256; 38+96+254+256; 38+111+163+254; 38+111+163+256; 38+111+254+256; 38+163+254+256; 91+96+111+163; 91+96+111+254; 91+96+111+256; 91+96+163+254; 91+96+163+256; 91+96+254+256; 91+111+163+254; 91+111+163+256; 91+111+254+256; 91+163+254+256; 96+111+163+254; 96+111+163+256; 96+111+254+256; 96+163+254+256; or 111+163+254+256 such as those described above.

In another aspect, the variant comprises or consists of the substitutions at positions corresponding to T231R+N233R and one of 27+33+38+91+96; 27+33+38+91+111; 27+33+38+91+163; 27+33+38+91+254; 27+33+38+91+256; 27+33+38+96+111; 27+33+38+96+163; 27+33+38+96+254; 27+33+38+96+256; 27+33+38+111+163; 27+33+38+111+254; 27+33+38+111+256; 27+33+38+163+254; 27+33+38+163+256; 27+33+38+254+256; 27+33+91+96+111; 27+33+91+96+163; 27+33+91+96+254; 27+33+91+96+256; 27+33+91+111+163; 27+33+91+111+254; 27+33+91+111+256; 27+33+91+163+254; 27+33+91+163+256; 27+33+91+254+256; 27+33+96+111+163; 27+33+96+111+254; 27+33+96+111+256; 27+33+96+163+254; 27+33+96+163+256; 27+33+96+254+256; 27+33+111+163+254; 27+33+111+163+256; 27+33+111+254+256; 27+33+163+254+256; 27+38+91+96+111; 27+38+91+96+163; 27+38+91+96+254; 27+38+91+96+256; 27+38+91+111+163; 27+38+91+111+254; 27+38+91+111+256; 27+38+91+163+254; 27+38+91+163+256; 27+38+91+254+256; 27+38+96+111+163; 27+38+96+111+254; 27+38+96+111+256; 27+38+96+163+254; 27+38+96+163+256; 27+38+96+254+256; 27+38+111+163+254; 27+38+111+163+256; 27+38+111+254+256; 27+38+163+254+256; 27+91+96+111+163; 27+91+96+111+254; 27+91+96+111+256; 27+91+96+163+254; 27+91+96+163+256; 27+91+96+254+256; 27+91+111+163+254; 27+91+111+163+256; 27+91+111+254+256; 27+91+163+254+256; 27+96+111+163+254; 27+96+111+163+256; 27+96+111+254+256; 27+96+163+254+256; 27+111+163+254+256; 33+38+91+96+111; 33+38+91+96+163; 33+38+91+96+254; 33+38+91+96+256; 33+38+91+111+163; 33+38+91+111+254; 33+38+91+111+256; 33+38+91+163+254; 33+38+91+163+256; 33+38+91+254+256; 33+38+96+111+163; 33+38+96+111+254; 33+38+96+111+256; 33+38+96+163+254; 33+38+96+163+256; 33+38+96+254+256; 33+38+111+163+254; 33+38+111+163+256; 33+38+111+254+256; 33+38+163+254+256; 33+91+96+111+163; 33+91+96+111+254; 33+91+96+111+256; 33+91+96+163+254; 33+91+96+163+256; 33+91+96+254+256; 33+91+111+163+254; 33+91+111+163+256; 33+91+111+254+256; 33+91+163+254+256; 33+96+111+163+254; 33+96+111+163+256; 33+96+111+254+256; 33+96+163+254+256; 33+111+163+254+256; 38+91+96+111+163; 38+91+96+111+254; 38+91+96+111+256; 38+91+96+163+254; 38+91+96+163+256; 38+91+96+254+256; 38+91+111+163+254; 38+91+111+163+256; 38+91+111+254+256; 38+91+163+254+256; 38+96+111+163+254; 38+96+111+163+256; 38+96+111+254+256; 38+96+163+254+256; 38+111+163+254+256; 91+96+111+163+254; 91+96+111+163+256; 91+96+111+254+256; 91+96+163+254+256; 91+111+163+254+256; or 96+111+163+254+256 such as those described above.

In another aspect, the variant comprises or consists of the substitutions at positions corresponding to T231R+N233R and one of 27+33+38+91+96+111; 27+33+38+91+96+163; 27+33+38+91+96+254; 27+33+38+91+96+256; 27+33+38+91+111+163; 27+33+38+91+111+254; 27+33+38+91+111+256; 27+33+38+91+163+254; 27+33+38+91+163+256; 27+33+38+91+254+256; 27+33+38+96+111+163; 27+33+38+96+111+254; 27+33+38+96+111+256; 27+33+38+96+163+254; 27+33+38+96+163+256; 27+33+38+96+254+256; 27+33+38+111+163+254; 27+33+38+111+163+256; 27+33+38+111+254+256; 27+33+38+163+254+256; 27+33+91+96+111+163; 27+33+91+96+111+254; 27+33+91+96+111+256; 27+33+91+96+163+254; 27+33+91+96+163+256; 27+33+91+96+254+256; 27+33+91+111+163+254; 27+33+91+111+163+256; 27+33+91+111+254+256; 27+33+91+163+254+256; 27+33+96+111+163+254; 27+33+96+111+163+256; 27+33+96+111+254+256; 27+33+96+163+254+256; 27+33+111+163+254+256; 27+38+91+96+111+163; 27+38+91+96+111+254; 27+38+91+96+111+256; 27+38+91+96+163+254; 27+38+91+96+163+256; 27+38+91+96+254+256; 27+38+91+111+163+254; 27+38+91+111+163+256; 27+38+91+111+254+256; 27+38+91+163+254+256; 27+38+96+111+163+254; 27+38+96+111+163+256; 27+38+96+111+254+256; 27+38+96+163+254+256; 27+38+111+163+254+256; 27+91+96+111+163+254; 27+91+96+111+163+256; 27+91+96+111+254+256; 27+91+96+163+254+256; 27+91+111+163+254+256; 27+96+111+163+254+256; 33+38+91+96+111+163; 33+38+91+96+111+254; 33+38+91+96+111+256; 33+38+91+96+163+254; 33+38+91+96+163+256; 33+38+91+96+254+256; 33+38+91+111+163+254; 33+38+91+111+163+256; 33+38+91+111+254+256; 33+38+91+163+254+256; 33+38+96+111+163+254; 33+38+96+111+163+256; 33+38+96+111+254+256; 33+38+96+163+254+256; 33+38+111+163+254+256; 33+91+96+111+163+254; 33+91+96+111+163+256; 33+91+96+111+254+256; 33+91+96+163+254+256; 33+91+111+163+254+256; 33+96+111+163+254+256; 38+91+96+111+163+254; 38+91+96+111+163+256; 38+91+96+111+254+256; 38+91+96+163+254+256; 38+91+111+163+254+256; 38+96+111+163+254+256; or 91+96+111+163+254+256 such as those described above.

In another aspect, the variant comprises or consists of the substitutions at positions corresponding to T231R+N233R and one of 27+33+38+91+96+111+163; 27+33+38+91+96+111+254; 27+33+38+91+96+111+256; 27+33+38+91+96+163+254; 27+33+38+91+96+163+256; 27+33+38+91+96+254+256; 27+33+38+91+111+163+254; 27+33+38+91+111+163+256; 27+33+38+91+111+254+256; 27+33+38+91+163+254+256; 27+33+38+96+111+163+254; 27+33+38+96+111+163+256; 27+33+38+96+111+254+256; 27+33+38+96+163+254+256; 27+33+38+111+163+254+256; 27+33+91+96+111+163+254; 27+33+91+96+111+163+256; 27+33+91+96+111+254+256; 27+33+91+96+163+254+256; 27+33+91+111+163+254+256; 27+33+96+111+163+254+256; 27+38+91+96+111+163+254; 27+38+91+96+111+163+256; 27+38+91+96+111+254+256; 27+38+91+96+163+254+256; 27+38+91+111+163+254+256; 27+38+96+111+163+254+256; 27+91+96+111+163+254+256; 33+38+91+96+111+163+254; 33+38+91+96+111+163+256; 33+38+91+96+111+254+256; 33+38+91+

96+163+254+256; 33+38+91+111+163+254+256; 33+38+ 96+111+163+254+256; 33+91+96+111+163+254+256; or 38+91+96+111+163+254+256 such as those described above.

In another aspect, the variant comprises or consists of the substitutions at positions corresponding to T231R+N233R and one of 27+33+38+91+96+111+163+254; 27+33+38+ 91+96+111+163+256; 27+33+38+91+96+111+254+256; 27+33+38+91+96+163+254+256; 27+33+38+91+111+ 163+254+256; 27+33+38+96+111+163+254+256; 27+33+ 91+96+111+163+254+256; 27+38+91+96+111+163+254+ 256; or 33+38+91+96+111+163+254+256; such as those described above.

In another aspect, the variant comprises or consists of the substitutions at positions corresponding to T231R+N233R and 27+33+38+91+96+111+163+254+256 such as those described above.

In another aspect, the variant comprises or consists of T231R+N233R and one or more (e.g., several) substitutions selected from the group consisting of D27R, N33Q, G38A, G91T, D96E, D111A, G163K, D254S, and P256T.

In another aspect, the variant comprises or consists of the substitutions at positions corresponding to T231R+N233R and one of D27R+N33Q; D27R+G38A; D27R+G91T; D27R+D96E; D27R+D111A; D27R+G163K; D27R+ D254S; D27R+P256T; N33Q+G38A; N33Q+G91T; N33Q+ D96E; N33Q+D111A; N33Q+G163K; N33Q+D254S; N33Q+P256T; G38A+G91T; G38A+D96E; G38A+D111A; G38A+G163K; G38A+D254S; G38A+P256T; G91T+ D96E; G91T+D111A; G91T+G163K; G91T+D254S; G91T+P256T; D96E+D111A; D96E+G163K; D96E+ D254S; D96E+P256T; D111A+G163K; D111A+D254S; D111A+P256T; G163K+D254S; G163K+P256T; or D254S+P256T of SEQ ID NO: 2.

In another aspect, the variant comprises or consists of the substitutions at positions corresponding to T231R+N233R and one of D27R+N33Q+G38A; D27R+N33Q+G91T; D27R+N33Q+D96E; D27R+N33Q+D111A; D27R+N33Q+ G163K; D27R+N33Q+D254S; D27R+N33Q+P256T; D27R+G38A+G91T; D27R+G38A+D96E; D27R+G38A+ D111A; D27R+G38A+G163K; D27R+G38A+D254S; D27R+G38A+P256T; D27R+G91T+D96E; D27R+G91T+ D111A; D27R+G91T+G163K; D27R+G91T+D254S; D27R+G91T+P256T; D27R+D96E+D111A; D27R+D96E+ G163K; D27R+D96E+D254S; D27R+D96E+P256T; D27R+D111A+G163K; D27R+D111A+D254S; D27R+ D111A+P256T; D27R+G163K+D254S; D27R+G163K+ P256T; D27R+D254S+P256T; N33Q+G38A+G91T; N33Q+G38A+D96E; N33Q+G38A+D111A; N33Q+ G38A+G163K; N33Q+G38A+D254S; N33Q+G38A+ P256T; N33Q+G91T+D96E; N33Q+G91T+D111A; N33Q+ G91T+G163K; N33Q+G91T+D254S; N33Q+G91T+ P256T; N33Q+D96E+D111A; N33Q+D96E+G163K; N33Q+D96E+D254S; N33Q+D96E+P256T; N33Q+ D111A+G163K; N33Q+D111A+D254S; N33Q+D111A+ P256T; N33Q+G163K+D254S; N33Q+G163K+P256T; N33Q+D254S+P256T; G38A+G91T+D96E; G38A+G91T+ D111A; G38A+G91T+G163K; G38A+G91T+D254S; G38A+G91T+P256T; G38A+D96E+D111A; G38A+ D96E+G163K; G38A+D96E+D254S; G38A+D96E+ P256T; G38A+D111A+G163K; G38A+D111A+D254S; G38A+D111A+P256T; G38A+G163K+D254S; G38A+ G163K+P256T; G38A+D254S+P256T; G91T+D96E+ D111A; G91T+D96E+G163K; G91T+D96E+D254S; G91T+D96E+P256T; G91T+D111A+G163K; G91T+ D111A+D254S; G91T+D111A+P256T; G91T+G163K+ D254S; G91T+G163K+P256T; G91T+D254S+P256T; D96E+D111A+G163K; D96E+D111A+D254S; D96E+ D111A+P256T; D96E+G163K+D254S; D96E+G163K+ P256T; D96E+D254S+P256T; D111A+G163K+D254S; D111A+G163K+P256T; D111A+D254S+P256T; or G163K+D254S+P256T of SEQ ID NO: 2.

In another aspect, the variant comprises or consists of the substitutions at positions corresponding to T231R+N233R and one of D27R+N33Q+G38A+G91T; D27R+N33Q+ G38A+D96E; D27R+N33Q+G38A+D111A; D27R+ N33Q+G38A+G163K; D27R+N33Q+G38A+D254S; D27R+N33Q+G38A+P256T; D27R+N33Q+G91T+D96E; D27R+N33Q+G91T+D111A; D27R+N33Q+G91T+ G163K; D27R+N33Q+G91T+D254S; D27R+N33Q+ G91T+P256T; D27R+N33Q+D96E+D111A; D27R+ N33Q+D96E+G163K; D27R+N33Q+D96E+D254S; D27R+N33Q+D96E+P256T; D27R+N33Q+D111A+ G163K; D27R+N33Q+D111A+D254S; D27R+N33Q+ D111A+P256T; D27R+N33Q+G163K+D254S; D27R+ N33Q+G163K+P256T; D27R+N33Q+D254S+P256T; D27R+G38A+G91T+D96E; D27R+G38A+G91T+D111A; D27R+G38A+G91T+G163K; D27R+G38A+G91T+ D254S; D27R+G38A+G91T+P256T; D27R+G38A+D96E+ D111A; D27R+G38A+D96E+G163K; D27R+G38A+ D96E+D254S; D27R+G38A+D96E+P256T; D27R+G38A+ D111A+G163K; D27R+G38A+D111A+D254S; D27R+ G38A+D111A+P256T; D27R+G38A+G163K+D254S; D27R+G38A+G163K+P256T; D27R+G38A+D254S+ P256T; D27R+G91T+D96E+D111A; D27R+G91T+D96E+ G163K; D27R+G91T+D96E+D254S; D27R+G91T+ D96E+P256T; D27R+G91T+D111A+G163K; D27R+ G91T+D111A+D254S; D27R+G91T+D111A+P256T; D27R+G91T+G163K+D254S; D27R+G91T+G163K+ P256T; D27R+G91T+D254S+P256T; D27R+D96E+ D111A+G163K; D27R+D96E+D111A+D254S; D27R+ D96E+D111A+P256T; D27R+D96E+G163K+D254S; D27R+D96E+G163K+P256T; D27R+D96E+D254S+ P256T; D27R+D111A+G163K+D254S; D27R+D111A+ G163K+P256T; D27R+D111A+D254S+P256T; D27R+ G163K+D254S+P256T; N33Q+G38A+G91T+D96E; N33Q+G38A+G91T+D111A; N33Q+G38A+G91T+ G163K; N33Q+G38A+G91T+D254S; N33Q+G38A+ G91T+P256T; N33Q+G38A+D96E+D111A; N33Q+ G38A+D96E+G163K; N33Q+G38A+D96E+D254S; N33Q+G38A+D96E+P256T; N33Q+G38A+D111A+ G163K; N33Q+G38A+D111A+D254S; N33Q+G38A+ D111A+P256T; N33Q+G38A+G163K+D254S; N33Q+ G38A+G163K+P256T; N33Q+G38A+D254S+P256T; N33Q+G91T+D96E+D111A; N33Q+G91T+D96E+ G163K; N33Q+G91T+D96E+D254S; N33Q+G91T+ D96E+P256T; N33Q+G91T+D111A+G163K; N33Q+ G91T+D111A+D254S; N33Q+G91T+D111A+P256T; N33Q+G91T+G163K+D254S; N33Q+G91T+G163K+ P256T; N33Q+G91T+D254S+P256T; N33Q+D96E+ D111A+G163K; N33Q+D96E+D111A+D254S; N33Q+ D96E+D111A+P256T; N33Q+D96E+G163K+D254S; N33Q+D96E+G163K+P256T; N33Q+D96E+D254S+ P256T; N33Q+D111A+G163K+D254S; N33Q+D111A+ G163K+P256T; N33Q+D111A+D254S+P256T; N33Q+ G163K+D254S+P256T; G38A+G91T+D96E+D111A; G38A+G91T+D96E+G163K; G38A+G91T+D96E+D254S; G38A+G91T+D96E+P256T; G38A+G91T+D111A+ G163K; G38A+G91T+D111A+D254S; G38A+G91T+ D111A+P256T; G38A+G91T+G163K+D254S; G38A+ G91T+G163K+P256T; G38A+G91T+D254S+P256T; G38A+D96E+D111A+G163K; G38A+D96E+D111A+ D254S; G38A+D96E+D111A+P256T; G38A+D96E+ G163K+D254S; G38A+D96E+G163K+P256T; G38A+

D96E+D254S+P256T; G38A+D111A+G163K+D254S; G38A+D111A+G163K+P256T; G38A+D111A+D254S+P256T; G38A+G163K+D254S+P256T; G91T+D96E+D111A+G163K; G91T+D96E+D111A+D254S; G91T+D96E+D111A+P256T; G91T+D96E+G163K+D254S; G91T+D96E+G163K+P256T; G91T+D96E+D254S+P256T; G91T+D111A+G163K+D254S; G91T+D111A+G163K+P256T; G91T+D111A+D254S+P256T; G91T+G163K+D254S+P256T; D96E+D111A+G163K+D254S; D96E+D111A+G163K+P256T; D96E+D111A+D254S+P256T; D96E+G163K+D254S+P256T; or D111A+G163K+D254S+P256T of SEQ ID NO: 2.

In another aspect, the variant comprises or consists of the substitutions at positions corresponding to T231R+N233R and one of D27R+N33Q+G38A+G91T+D96E; D27R+N33Q+G38A+G91T+D111A; D27R+N33Q+G38A+G91T+G163K; D27R+N33Q+G38A+G91T+D254S; D27R+N33Q+G38A+G91T+P256T; D27R+N33Q+G38A+D96E+D111A; D27R+N33Q+G38A+D96E+G163K; D27R+N33Q+G38A+D96E+D254S; D27R+N33Q+G38A+D96E+P256T; D27R+N33Q+G38A+D111A+G163K; D27R+N33Q+G38A+D111A+D254S; D27R+N33Q+G38A+D111A+P256T; D27R+N33Q+G38A+G163K+D254S; D27R+N33Q+G38A+G163K+P256T; D27R+N33Q+G38A+D254S+P256T; D27R+N33Q+G91T+D96E+D111A; D27R+N33Q+G91T+D96E+G163K; D27R+N33Q+G91T+D96E+D254S; D27R+N33Q+G91T+D96E+P256T; D27R+N33Q+G91T+D111A+G163K; D27R+N33Q+G91T+D111A+D254S; D27R+N33Q+G91T+D111A+P256T; D27R+N33Q+G91T+G163K+D254S; D27R+N33Q+G91T+G163K+P256T; D27R+N33Q+G91 T+D254S+P256T; D27R+N33Q+D96E+D111A+G163K; D27R+N33Q+D96E+D111A+D254S; D27R+N33Q+D96E+D111A+P256T; D27R+N33Q+D96E+G163K+D254S; D27R+N33Q+D96E+G163K+P256T; D27R+N33Q+D96E+D254S+P256T; D27R+N33Q+D111A+G163K+D254S; D27R+N33Q+D111A+G163K+P256T; D27R+N33Q+D111A+D254S+P256T; D27R+N33Q+G163K+D254S+P256T; D27R+G38A+G91T+D96E+D111A; D27R+G38A+G91T+D96E+G163K; D27R+G38A+G91T+D96E+D254S; D27R+G38A+G91T+D96E+P256T; D27R+G38A+G91T+D111A+G163K; D27R+G38A+G91T+D111A+D254S; D27R+G38A+G91T+D111A+P256T; D27R+G38A+G91T+G163K+D254S; D27R+G38A+G91T+G163K+P256T; D27R+G38A+G91T+D254S+P256T; D27R+G38A+D96E+D111A+G163K; D27R+G38A+D96E+D111A+D254S; D27R+G38A+D96E+D111A+P256T; D27R+G38A+D96E+G163K+D254S; D27R+G38A+D96E+G163K+P256T; D27R+G38A+D96E+D254S+P256T; D27R+G38A+D111A+G163K+D254S; D27R+G38A+D111A+G163K+P256T; D27R+G38A+D111A+D254S+P256T; D27R+G38A+G163K+D254S+P256T; D27R+G91T+D96E+D111A+G163K; D27R+G91T+D96E+D111A+D254S; D27R+G91T+D96E+D111A+P256T; D27R+G91T+D96E+G163K+D254S; D27R+G91T+D96E+G163K+P256T; D27R+G91T+D96E+D254S+P256T; D27R+G91T+D111A+G163K+D254S; D27R+G91T+D111A+G163K+P256T; D27R+G91T+D111A+D254S+P256T; D27R+G91T+G163K+D254S+P256T; D27R+D96E+D111A+G163K+D254S; D27R+D96E+D111A+G163K+P256T; D27R+D96E+D111A+D254S+P256T; D27R+D96E+G163K+D254S+P256T; D27R+D111A+G163K+D254S+P256T; N33Q+G38A+G91T+D96E+D111A; N33Q+G38A+G91T+D96E+G163K; N33Q+G38A+G91T+D96E+D254S; N33Q+G38A+G91T+D96E+P256T; N33Q+G38A+G91T+D111A+G163K; N33Q+G38A+G91T+D111A+D254S; N33Q+G38A+G91T+D111A+P256T; N33Q+G38A+G91T+G163K+D254S; N33Q+G38A+G91T+G163K+P256T; N33Q+G38A+G91T+D254S+P256T; N33Q+G38A+D96E+D111A+G163K; N33Q+G38A+D96E+D111A+D254S; N33Q+G38A+D96E+D111A+P256T; N33Q+G38A+D96E+G163K+D254S; N33Q+G38A+D96E+G163K+P256T; N33Q+G38A+D96E+D254S+P256T; N33Q+G38A+D111A+G163K+D254S; N33Q+G38A+D111A+G163K+P256T; N33Q+G38A+D111A+D254S+P256T; N33Q+G38A+G163K+D254S+P256T; N33Q+G91T+D96E+D111A+G163K; N33Q+G91T+D96E+D111A+D254S; N33Q+G91T+D96E+D111A+P256T; N33Q+G91T+D96E+G163K+D254S; N33Q+G91T+D96E+G163K+P256T; N33Q+G91T+D96E+D254S+P256T; N33Q+G91T+D111A+G163K+D254S; N33Q+G91T+D111A+G163K+P256T; N33Q+G91T+D111A+D254S+P256T; N33Q+G91T+G163K+D254S+P256T; N33Q+D96E+D111A+G163K+D254S; N33Q+D96E+D111A+G163K+P256T; N33Q+D96E+D111A+D254S+P256T; N33Q+D96E+G163K+D254S+P256T; N33Q+D111A+G163K+D254S+P256T; G38A+G91T+D96E+D111A+G163K; G38A+G91T+D96E+D111A+D254S; G38A+G91T+D96E+D111A+P256T; G38A+G91T+D96E+G163K+D254S; G38A+G91T+D96E+G163K+P256T; G38A+G91T+D96E+D254S+P256T; G38A+G91T+D111A+G163K+D254S; G38A+G91T+D111A+G163K+P256T; G38A+G91T+D111A+D254S+P256T; G38A+G91T+G163K+D254S+P256T; G38A+D96E+D111A+G163K+D254S; G38A+D96E+D111A+G163K+P256T; G38A+D96E+D111A+D254S+P256T; G38A+D96E+G163K+D254S+P256T; G38A+D111A+G163K+D254S+P256T; G91T+D96E+D111A+G163K+D254S; G91T+D96E+D111A+G163K+P256T; G91T+D96E+D111A+D254S+P256T; G91T+D96E+G163K+D254S+P256T; G91T+D111A+G163K+D254S+P256T; or D96E+D111A+G163K+D254S+P256T of SEQ ID NO: 2.

In another aspect, the variant comprises or consists of the substitutions at positions corresponding to T231R+N233R and one of D27R+N33Q+G38A+G91T+D96E+D111A; D27R+N33Q+G38A+G91T+D96E+G163K; D27R+N33Q+G38A+G91T+D96E+D254S; D27R+N33Q+G38A+G91T+D96E+P256T; D27R+N33Q+G38A+G91T+D111A+G163K; D27R+N33Q+G38A+G91T+D111A+D254S; D27R+N33Q+G38A+G91T+D111A+P256T; D27R+N33Q+G38A+G91T+G163K+D254S; D27R+N33Q+G38A+G91T+G163K+P256T; D27R+N33Q+G38A+G91T+D254S+P256T; D27R+N33Q+G38A+D96E+D111A+G163K; D27R+N33Q+G38A+D96E+D111A+D254S; D27R+N33Q+G38A+D96E+D111A+P256T; D27R+N33Q+G38A+D96E+G163K+D254S; D27R+N33Q+G38A+D96E+G163K+P256T; D27R+N33Q+G38A+D96E+D254S+P256T; D27R+N33Q+G38A+D111A+G163K+D254S; D27R+N33Q+G38A+D111A+G163K+P256T; D27R+N33Q+G38A+D111A+D254S+P256T; D27R+N33Q+G38A+G163K+D254S+P256T; D27R+N33Q+G91T+D96E+D111A+G163K; D27R+N33Q+G91T+D96E+D111A+D254S; D27R+N33Q+G91T+D96E+D111A+P256T; D27R+N33Q+G91T+D96E+G163K+D254S; D27R+N33Q+G91T+D96E+G163K+P256T; D27R+N33Q+G91T+D96E+D254S+P256T; D27R+N33Q+G91T+D111A+G163K+D254S; D27R+N33Q+G91T+D111A+G163K+P256T; D27R+N33Q+G91T+D111A+D254S+P256T; D27R+N33Q+G91T+G163K+D254S+P256T; D27R+N33Q+D96E+D111A+G163K+D254S; D27R+N33Q+D96E+D111A+G163K+P256T; D27R+N33Q+D96E+D111A+

D254S+P256T; D27R+N33Q+D96E+G163K+D254S+P256T; D27R+N33Q+D111A+G163K+D254S+P256T; D27R+G38A+G91T+D96E+D111A+G163K; D27R+G38A+G91T+D96E+D111A+D254S; D27R+G38A+G91T+D96E+D111A+P256T; D27R+G38A+G91T+D96E+G163K+D254S; D27R+G38A+G91T+D96E+G163K+P256T; D27R+G38A+G91T+D96E+D254S+P256T; D27R+G38A+G91T+D111A+G163K+D254S; D27R+G38A+G91T+D111A+G163K+P256T; D27R+G38A+G91T+D111A+D254S+P256T; D27R+G38A+G91T+G163K+D254S+P256T; D27R+G38A+D96E+D111A+G163K+D254S; D27R+G38A+D96E+D111A+G163K+P256T; D27R+G38A+D96E+D111A+D254S+P256T; D27R+G38A+D96E+G163K+D254S+P256T; D27R+G38A+D111A+G163K+D254S+P256T; D27R+G91T+D96E+D111A+G163K+D254S; D27R+G91T+D96E+D111A+G163K+P256T; D27R+G91T+D96E+D111A+D254S+P256T; D27R+G91T+D96E+G163K+D254S+P256T; D27R+G91T+D111A+G163K+D254S+P256T; D27R+D96E+D111A+G163K+D254S+P256T; N33Q+G38A+G91T+D96E+D111A+G163K; N33Q+G38A+G91T+D96E+D111A+D254S; N33Q+G38A+G91T+D96E+D111A+P256T; N33Q+G38A+G91T+D96E+G163K+D254S; N33Q+G38A+G91T+D96E+G163K+P256T; N33Q+G38A+G91T+D96E+D254S+P256T; N33Q+G38A+G91T+D111A+G163K+D254S; N33Q+G38A+G91T+D111A+G163K+P256T; N33Q+G38A+G91T+D111A+D254S+P256T; N33Q+G38A+G91T+G163K+D254S+P256T; N33Q+G38A+D96E+D111A+G163K+D254S; N33Q+G38A+D96E+D111A+G163K+P256T; N33Q+G38A+D96E+D111A+D254S+P256T; N33Q+G38A+D96E+G163K+D254S+P256T; N33Q+G38A+D111A+G163K+D254S+P256T; N33Q+G91T+D96E+D111A+G163K+D254S; N33Q+G91T+D96E+D111A+G163K+P256T; N33Q+G91T+D96E+D111A+D254S+P256T; N33Q+G91T+D96E+G163K+D254S+P256T; N33Q+G91T+D111A+G163K+D254S+P256T; N33Q+D96E+D111A+G163K+D254S+P256T; G38A+G91T+D96E+D111A+G163K+D254S; G38A+G91T+D96E+D111A+G163K+P256T; G38A+G91T+D96E+D111A+D254S+P256T; G38A+G91T+D96E+G163K+D254S+P256T; G38A+G91T+D111A+G163K+D254S+P256T; G38A+D96E+D111A+G163K+D254S+P256T; or G91T+D96E+D111A+G163K+D254S+P256T of SEQ ID NO: 2.

In another aspect, the variant comprises or consists of the substitutions at positions corresponding to T231R+N233R and one of D27R+N33Q+G38A+G91T+D96E+D111A+G163K; D27R+N33Q+G38A+G91T+D96E+D111A+D254S; D27R+N33Q+G38A+G91T+D96E+D111A+P256T; D27R+N33Q+G38A+G91T+D96E+G163K+D254S; D27R+N33Q+G38A+G91T+D96E+G163K+P256T; D27R+N33Q+G38A+G91T+D96E+D254S+P256T; D27R+N33Q+G38A+G91T+D111A+G163K+D254S; D27R+N33Q+G38A+G91T+D111A+G163K+P256T; D27R+N33Q+G38A+G91T+D111A+D254S+P256T; D27R+N33Q+G38A+G91T+G163K+D254S+P256T; D27R+N33Q+G38A+D96E+D111A+G163K+D254S; D27R+N33Q+G38A+D96E+D111A+G163K+P256T; D27R+N33Q+G38A+D96E+D111A+D254S+P256T; D27R+N33Q+G38A+D96E+G163K+D254S+P256T; D27R+N33Q+G38A+D111A+G163K+D254S+P256T; D27R+N33Q+G91T+D96E+D111A+G163K+D254S; D27R+N33Q+G91T+D96E+D111A+G163K+P256T; D27R+N33Q+G91T+D96E+D111A+D254S+P256T; D27R+N33Q+G91T+D96E+G163K+D254S+P256T; D27R+N33Q+G91T+D111A+G163K+D254S+P256T; D27R+N33Q+D96E+D111A+G163K+D254S+P256T; D27R+G38A+G91T+D96E+D111A+G163K+D254S; D27R+G38A+G91T+D96E+D111A+G163K+P256T; D27R+G38A+G91T+D96E+D111A+D254S+P256T; D27R+G38A+G91T+D96E+G163K+D254S+P256T; D27R+G38A+G91T+D111A+G163K+D254S+P256T; D27R+G38A+D96E+D111A+G163K+D254S+P256T; D27R+G91T+D96E+D111A+G163K+D254S+P256T; N33Q+G38A+G91T+D96E+D111A+G163K+D254S; N33Q+G38A+G91T+D96E+D111A+G163K+P256T; N33Q+G38A+G91T+D96E+D111A+D254S+P256T; N33Q+G38A+G91T+D96E+G163K+D254S+P256T; N33Q+G38A+G91T+D111A+G163K+D254S+P256T; N33Q+G38A+D96E+D111A+G163K+D254S+P256T; N33Q+G91T+D96E+D111A+G163K+D254S+P256T; or G38A+G91T+D96E+D111A+G163K+D254S+P256T of SEQ ID NO: 2.

In another aspect, the variant comprises or consists of the substitutions at positions corresponding to T231R+N233R and one of D27R+N33Q+G38A+G91T+D96E+D111A+G163K+D254S; D27R+N33Q+G38A+G91T+D96E+D111A+G163K+P256T; D27R+N33Q+G38A+G91T+D96E+D111A+D254S+P256T; D27R+N33Q+G38A+G91T+D96E+G163K+D254S+P256T; D27R+N33Q+G38A+G91T+D111A+G163K+D254S+P256T; D27R+N33Q+G38A+D96E+D111A+G163K+D254S+P256T; D27R+N33Q+G91T+D96E+D111A+G163K+D254S+P256T; D27R+G38A+G91T+D96E+D111A+G163K+D254S+P256T; or N33Q+G38A+G91T+D96E+D111A+G163K+D254S+P256T of SEQ ID NO: 2.

In another aspect, the variant comprises or consists of the substitutions at positions corresponding to T231R+N233R and D27R+N33Q+G38A+G91T+D96E+D111A+G163K+D254S+P256T of SEQ ID NO: 2.

In another aspect, the variants comprise or consist of substitutions at positions corresponding to the following of SEQ ID NO: 2:
D96E+T231R+N233R;
N33Q+D96E+T231R+N233R;
N33Q+D111A+T231R+N233R;
N33Q+T231R+N233R+P256T;
N33Q+G38A+G91T+G163K+T231R+N233R+D254S;
N33Q+G38A+G91T+D96E+D111A+G163K+T231R+N233R+D254S+P256T;
D27R+N33Q+G38A+D96E+D111A+G163K+T231R+N233R+D254S+P256T;
D27R+N33Q+G38A+G91T+D96E+D111A+G163K+T231R+N233R+P256T;
D27R+N33Q+G38A+G91T+D96E+D111A+G163K+T231R+N233R+D254S;
D27R+G38A+G91T+D96E+D111A+G163K+T231R+N233R+D254S+P256T;
D96E+T231R+N233R+D254S;
T231R+N233R+D254S+P256T;
G163K+T231R+N233R+D254S;
D27R+N33Q+G38A+G91T+D96E+G163K+T231R+N233R+D254S+P256T;
D27R+G91T+D96E+D111A+G163K+T231R+N233R+D254S+P256T;
D96E+G163K+T231R+N233R+D254S;
D27R+G163K+T231R+N233R+D254S;
D27R+G38A+G91T+D96E+D111A+G163K+T231R+N233R+D254S;
D27R+G38A+G91T+D96E+G163K+T231R+N233R+D254S+P256T;
D27R+G38A+D96E+D111A+G163K+T231R+N233R+D254S+P256T;

D27R+D96E+G163K+T231R+N233R+D254S;
D27R+D96E+D111A+G163K+T231R+N233R+D254S+P256T;
D27R+G38A+D96E+G163K+T231R+N233R+D254S+P256T;
D27R+G38A+D96E+D111A+G163K+T231R+N233R+D254S;
D27R+D96E+G163K+T231R+N233R;
D27R+D96E+G163K+T231R+N233R+D254S+P256T;
D27R+D96E+D111A+G163D+T231R+N233R+D254S+P256T;
D27R+D96E+D111A+G163K+T231R+N233R+D254S;
D27R+D96E+D111A+G163K+T231R+N233R+P256T;
D27R+D111A+G163K+T231R+N233R+D254S+P256T;
D96E+D111A+G163K+T231R+N233R+D254S+P256T;
D27R+G38A+D96E+D111A+G163K+T231R+N233R+P256T;
D27R+G38A+D96E+D111A+T231R+N233R+D254S+P256T;
D27R+G38A+D96E+G163K+T231R+N233R+D254S+P256T;
D27R+D96E+G163K+T231R+N233R+D254S+P256T;
D27R+N33Q+G38A+G91T+D111A+G163K+T231R+N233R+D254S+P256T;
D27R+G38A+D111A+G163K+T231R+N233R+D254S+P256T;
D111A+G163K+T231R+N233R+D254S+P256T;
D111A+T231R+N233R;
D111A+T231R+N233R+D254S+P256T;
D27R+D96E+D111A+G163K+T231R+N233R;
D27R+D96E+D111A+T231R+N233R;
D27R+G38A+D96E+D111A+G163K+T231R+N233R+D254S+P256T;
D27R+N33Q+G38A+D96E+D111A+T231R+N233R+D254S+P256T;
D27R+G38A+D96E+D111A+G163K+E210Q+T231R+N233R+D254S+P256T;
D27R+T231R+N233R+D254S+P256T;
D96E+D111A+G163K+T231R+N233R;
D96E+D111A+G163K+T231R+N233R+D254S+P256T;
D96E+D111A+G163K+T231R+N233R+P256T;
D96E+D111A+T231R+N233R;
D96E+D111A+T231R+N233R+D254S;
D96E+D111A+T231R+N233R+P256T;
D96E+G163K+T231R+N233R+D254S+P256T;
D96E+T231R+N233R+D254S+P256T;
D96E+T231R+N233R+P256T;
G38A+D96E+D111A+T231R+N233R;
G91T+D96E+D111A+G163K+T231R+N233R+D254S+P256T;
G91T+D96E+D111A+T231R+N233R;
G91T+D96E+T231R+N233R;
G91T+T231R+N233R+D254S+P256T;
N33Q+D96E+D111A+G163K+T231R+N233R+D254S+P256T;
T231R+N233R+D254S+P256T; or
T231R+N233R+P256T.

The variants may further comprise one or more additional substitutions at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for lipase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The variants may consist or contain at least 50%, at least 55%, at least 60%, at least 65%, at least 70%, at least 75%, at least 80%, at least 85%, at least 90%, or at least 95% of the number of amino acids of SEQ ID NO: 2.

In an embodiment, the variant has improved stability in detergent with protease present compared to the parent lipase.

In an embodiment, the variant has improved detergent stability compared to the parent lipase.

In an embodiment, the variant has improved protease stability compared to the parent lipase.

In an embodiment, the variant has improved chemical stability compared to the parent lipase.

In an embodiment, the variant has improved oxidation stability compared to the parent lipase.

In an embodiment, the variant has improved pH stability compared to the parent lipase.

In an embodiment, the variant has improved stability under storage conditions compared to the parent lipase.

In an embodiment, the variant has improved thermostability compared to the parent lipase.

Parent Lipases

The parent lipase may be (a) a polypeptide having at least 60% sequence identity to the polypeptide of SEQ ID NO: 2; (b) a polypeptide encoded by a polynucleotide that hybridizes under low stringency conditions with (i) the polypeptide coding sequence of SEQ ID NO: 1, (ii) the full-length complement of (i); or (c) a polypeptide encoded by a polynucleotide having at least 60% sequence identity to the polypeptide coding sequence of SEQ ID NO: 1.

In an aspect, the parent has a sequence identity to the polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from the polypeptide of SEQ ID NO: 2.

In another aspect, the parent comprises or consists of the amino acid sequence of SEQ ID NO: 2.

In another aspect, the parent is a fragment of the polypeptide of SEQ ID NO: 2 containing at least 50%, at least 55%, at least 60%, at least 65%, at least 70%, at least 75%, at least 80%, at least 85%, at least 90%, or at least 95% of the number of amino acids of SEQ ID NO: 2.

In another embodiment, the parent is an allelic variant of the polypeptide of SEQ ID NO: 2.

In another aspect, the parent is encoded by a polynucleotide that hybridizes under very low stringency conditions, low stringency conditions, medium stringency conditions, medium-high stringency conditions, high stringency conditions, or very high stringency conditions with (i) the polypeptide coding sequence of SEQ ID NO: 1, (ii) the full-length complement of (i) (Sambrook et al., 1989, *Molecular Cloning, A Laboratory Manual,* 2d edition, Cold Spring Harbor, New York).

The polynucleotide of SEQ ID NO: 1 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the polypeptide coding sequence of SEQ ID NO: 1. In another aspect, the nucleic acid probe is at least 50%, at least 55%, at least 60%, at least 65%, at least 70%, at least 75%, at least 80%, at least 85%, at least 90%, or at least 95% of the number of nucleotides of SEQ ID NO: 1. In another aspect, the nucleic acid probe is a polynucleotide that encodes the polypeptide of SEQ ID NO: 2; the polypeptide thereof; or a fragment thereof. In another aspect, the nucleic acid probe is SEQ ID NO: 1.

In another embodiment, the parent is encoded by a polynucleotide having a sequence identity to the polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial lipase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus, Streptomyces* or *Thermobifida* lipase, or a Gram-negative bacterial polypeptide such as a *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma* lipase.

In one aspect, the parent is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* lipase.

In another aspect, the parent is a *Streptococcus equisimilis*, *Streptococcus pyogenes*, *Streptococcus uberis*, or *Streptococcus equi* subsp. *Zooepidemicus* lipase.

In another aspect, the parent is a *Streptomyces achromogenes*, *Streptomyces avermitilis*, *Streptomyces coelicolor*, *Streptomyces griseus*, or *Streptomyces lividans* lipase.

In another aspect, the parent is a *Thermobifida alba* or *Thermobifida fusca* (formerly known as *Thermomonaspora fusca*) lipase.

The parent may be a fungal lipase. For example, the parent may be a yeast lipase such as a *Candida*, *Kluyveromyces*, *Pichia*, *Saccharomyces*, *Schizosaccharomyces*, or *Yarrowia* lipase; or a filamentous fungal lipase such as an *Acremonium*, *Agaricus*, *Alternaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* lipase.

In another aspect, the parent is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* lipase.

In another aspect, the parent is an *Acremonium cellulolyticus*, *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia setosa*, *Thielavia spededonium*, *Thielavia subthermophila*, *Thielavia terrestris*, *Trichoderma harzianum*, *Trichoderma koningii*, *Trichoderma longibrachiatum*, *Trichoderma reesei*, or *Trichoderma viride* lipase.

In another aspect, the parent is a *Thermomyces lanuginosus* lipase, e.g., the lipase of SEQ ID NO: 2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Lipase Particles

The lipase variants comprised in the water-soluble film of the invention may be present as lipase particles. The lipase particles may even contain one or more Additional Enzymes, as described below.

Lipase particles are any form of lipase variant in a solid particulate form. That can be as lipase crystals, lipase precipitate, spray or freeze-dried lipase or any form of granulated lipase, either as a powder or a suspension in liquid. Typically the particle size, measured as equivalent spherical diameter (volume based average particle size), of the lipase particles is below 2 mm, preferably below 1 mm, below 0.5 mm, below 0.25 mm, or below 0.1 mm; and above 0.05 µm, preferably above 0.1 µm, above 0.5 µm, above 1 µm, above 5 µm or above 10 µm.

In a preferred embodiment, the particle size of the lipase particles is from 0.5 µm to 100 µm.

The lipase particles contain at least 1% w/w lipase protein, preferably at least 5% w/w lipase protein, at least 10% w/w lipase protein, at least 20% w/w lipase protein, at least 30% w/w lipase protein, at least 40% w/w lipase protein, at least 50% w/w lipase protein, at least 60% w/w lipase protein, at least 70% w/w lipase protein, at least 80% w/w lipase protein, or at least 90% w/w lipase protein.

In a preferred embodiment, the lipase particles are lipase crystals, or the lipase protein is on a crystalline form.

Enzyme crystallization may be carried out in a number of ways, as known in the art (e.g., as described in WO 91/09943 or WO 94/22903).

The lipase may be formulated in the lipase particle as known in the art for solid enzyme formulations, such as formulations for reducing dust, improving stability and/or modifying release rate of the enzyme. The lipase particle may also be formulated in a matrix or coated with agents suppressing dissolution of the enzyme particle in the PVOH/film solution used for preparing the water-soluble film.

The lipase molecules on the surface of the lipase particles may also be cross-linked, like CLECs (Cross-Linked Enzyme Crystals) or CLEA (Cross-Linked Enzyme Aggregate).

Water-soluble Film

Water-soluble films, optional ingredients for use therein, and methods of making the same are well known in the art. In one class of embodiments, the water-soluble film includes PVOH. PVOH is a synthetic resin generally prepared by the alcoholysis, usually termed hydrolysis or saponification, of polyvinyl acetate. Fully hydrolyzed PVOH, wherein virtually all the acetate groups have been converted to alcohol groups, is a strongly hydrogen-bonded, highly crystalline polymer which dissolves only in hot water—greater than about 140° F. (60° C.). If a sufficient number of acetate groups are allowed to remain after the hydrolysis of polyvinyl acetate, the PVOH polymer then being known as partially hydrolyzed, it is more weakly hydrogen-bonded and less crystalline and is soluble in cold water—less than about 50° F. (10° C.). An intermediate cold/hot water-soluble film can include, for example, intermediate partially-hydrolyzed PVOH (e.g., with degrees of hydrolysis of about 94% to about 98%), and is readily soluble only in warm water—e.g., rapid dissolution at temperatures of about 40° C. and greater. Both fully and partially hydrolyzed PVOH types are commonly referred to as PVOH homopolymers although the partially hydrolyzed type is technically a vinyl alcohol-vinyl acetate copolymer.

The degree of hydrolysis of the PVOH included in the water-soluble films of the present disclosure can be about 75% to about 99%. As the degree of hydrolysis is reduced, a film made from the resin will have reduced mechanical strength but faster solubility at temperatures below about 20° C. As the degree of hydrolysis increases, a film made from the resin will tend to be mechanically stronger and the thermoformability will tend to decrease. The degree of hydrolysis of the PVOH can be chosen such that the water-solubility of the resin is temperature dependent, and thus the solubility of a film made from the resin, compatibilizing agent, and additional ingredients is also influenced. In one class of embodiments the film is cold water-soluble. A cold water-soluble film, soluble in water at a temperature of less than 10° C., can include PVOH with a degree of hydrolysis in a range of about 75% to about 90%, or in a range of about 80% to about 90%, or in a range of about 85% to about 90%. In another class of embodiments the film is hot water-soluble. A hot water-soluble film, soluble in water at a temperature of at least about 60° C., can include PVOH with a degree of hydrolysis of at least about 98%.

Other film-forming resins for use in addition to or in an alternative to PVOH can include, but are not limited to, modified polyvinyl alcohols, polyacrylates, water-soluble acrylate copolymers, polyacrylates, polyacryamides, polyvinyl pyrrolidone, pullulan, water-soluble natural polymers including, but not limited to, guar gum, xanthan gum, carrageenan, and starch, water-soluble polymer derivatives including, but not limited to, ethoxylated starch and hydroxypropylated starch, poly(sodium acrylamido-2-methylpropane sulfonate), polymonomethylmaleate, copolymers thereof, and combinations of any of the foregoing. In one class of embodiments, the film-forming resin is a terpolymer consisting of vinyl alcohol, vinyl acetate, and sodium acrylamido-2-methylpropanesulfonate. Unexpectedly, water-soluble films based on a vinyl alcohol, vinyl acetate, and sodium acrylamido-2-methylpropanesulfonate terpolymer have demonstrated a high percent recovery of enzyme.

The water-soluble resin can be included in the water-soluble film in any suitable amount, for example an amount in a range of about 35 wt % to about 90 wt %. The preferred weight ratio of the amount of the water-soluble resin as compared to the combined amount of all enzymes, enzyme stabilizers, and secondary additives can be any suitable ratio, for example a ratio in a range of about 0.5 to about 5, or about 1 to 3, or about 1 to 2.

Water-soluble resins for use in the films described herein (including, but not limited to PVOH resins) can be characterized by any suitable viscosity for the desired film properties, optionally a viscosity in a range of about 5.0 to about 30.0 cP, or about 10.0 cP to about 25 cP. The viscosity of a PVOH resin is determined by measuring a freshly made solution using a Brookfield LV type viscometer with UL adapter as described in British Standard EN ISO 15023-2: 2006 Annex E Brookfield Test method. It is international practice to state the viscosity of 4% aqueous polyvinyl alcohol solutions at 20° C. All PVOH viscosities specified herein in cP should be understood to refer to the viscosity of 4% aqueous polyvinyl alcohol solution at 20° C., unless specified otherwise.

It is well known in the art that the viscosity of a PVOH resin is correlated with the weight average molecular weight ($\overline{M}w$) of the same PVOH resin, and often the viscosity is used as a proxy for $\overline{M}w$. Thus, the weight average molecular weight of the water-soluble resin optionally can be in a range of about 35,000 to about 190,000, or about 80,000 to about 160,000. The molecular weight of the resin need only be sufficient to enable it to be molded by suitable techniques to form a thin plastic film.

The water-soluble films according to the present disclosure may include other optional additive ingredients including, but not limited to, plasticizers, surfactants, defoamers, film formers, antiblocking agents, internal release agents, anti-yellowing agents and other functional ingredients, for example in amounts suitable for their intended purpose.

Water is recognized as a very efficient plasticizer for PVOH and other polymers; however, the volatility of water makes its utility limited since polymer films need to have at least some resistance (robustness) to a variety of ambient conditions including low and high relative humidity. Glycerin is much less volatile than water and has been well established as an effective plasticizer for PVOH and other polymers. Glycerin or other such liquid plasticizers by themselves can cause surface "sweating" and greasiness if the level used in the film formulation is too high. This can lead to problems in a film such as unacceptable feel to the hand of the consumer and even blocking of the film on the roll or in stacks of sheets if the sweating is not mitigated in some manner, such as powdering of the surface. This could be characterized as over plasticization. However, if too little plasticizer is added to the film the film may lack sufficient ductility and flexibility for many end uses, for example to be converted into a final use format such as pouches.

Plasticizers for use in water-soluble films of the present disclosure include, but are not limited to, sorbitol, glycerol, diglycerol, propylene glycol, ethylene glycol, diethyleneglycol, triethylene glycol, tetraethyleneglycol, polyethylene glycols up to MW 400, 2 methyl 1, 3 propane diol, lactic acid, monoacetin, triacetin, triethyl citrate, 1,3-butanediol, trimethylolpropane (TMP), polyether triol, and combinations thereof. Polyols, as described above, are generally useful as plasticizers. As less plasticizer is used, the film can become more brittle, whereas as more plasticizer is used the film can lose tensile strength. Plasticizers can be included in the water-soluble films in an amount in a range of about 25 phr to about 50 phr, or from about 30 phr to about 45 phr, or from about 32 phr to about 42 phr, for example.

Surfactants for use in water-soluble films are well known in the art. Optionally, surfactants are included to aid in the dispersion of the resin solution upon casting. Suitable surfactants for water-soluble films of the present disclosure include, but are not limited to, dialkyl sulfosuccinates, lactylated fatty acid esters of glycerol and propylene glycol, lactylic esters of fatty acids, sodium alkyl sulfates, polysorbate 20, polysorbate 60, polysorbate 65, polysorbate 80, alkyl polyethylene glycol ethers, lecithin, acetylated fatty acid esters of glycerol and propylene glycol, sodium lauryl sulfate, acetylated esters of fatty acids, myristyl dimethylamine oxide, trimethyl tallow alkyl ammonium chloride, quaternary ammonium compounds, salts thereof and combinations of any of the forgoing. Thus, surfactants can be included in the water-soluble films in an amount of less than about 2 phr, for example less than about 1 phr, or less than about 0.5 phr, for example.

One type of secondary component contemplated for use is a defoamer. Defoamers can aid in coalescing of foam bubbles. Suitable defoamers for use in water-soluble films according to the present disclosure include, but are not limited to, hydrophobic silicas, for example silicon dioxide or fumed silica in fine particle sizes, including Foam Blast® defoamers available from Emerald Performance Materials, including Foam Blast® 327, Foam Blast® UVD, Foam Blast® 163, Foam Blast® 269, Foam Blast® 338, Foam Blast® 290, Foam Blast® 332, Foam Blast® 349, Foam Blast® 550 and Foam Blast® 339, which are proprietary, non-mineral oil defoamers. In embodiments, defoamers can be used in an amount of 0.5 phr, or less, for example, 0.05 phr, 0.04 phr, 0.03 phr, 0.02 phr, or 0.01 phr. Preferably, significant amounts of silicon dioxide will be avoided, in order to avoid stress whitening.

Processes for making water-soluble articles, including films, include casting, blow-molding, extrusion and blown extrusion, as known in the art. One contemplated class of embodiments is characterized by the water-soluble film described herein being formed by casting, for example, by admixing the ingredients described herein with water to create an aqueous mixture, for example a solution with optionally dispersed solids, applying the mixture to a surface, and drying off water to create a film. Similarly, other compositions can be formed by drying the mixture while it is confined in a desired shape.

In one contemplated class of embodiments, the water-soluble film is formed by casting a water-soluble mixture wherein the water-soluble mixture is prepared according to the steps of:
(a) providing a mixture of water-soluble resin, water, and any optional additives excluding plasticizers;
(b) boiling the mixture for 30 minutes;
(c) degassing the mixture in an oven at a temperature of at least 40° C.; optionally in a range of 40° C. to 70° C., e.g., about 65° C.;
(d) adding one or more enzymes, plasticizer, and additional water to the mixture at a temperature of 65° C. or less; and
(e) stirring the mixture without vortex until the mixture appears substantially uniform in color and consistency; optionally for a time period in a range of 30 minutes to 90 minutes, optionally at least 1 hour; and
(f) casting the mixture promptly after the time period of stirring (e.g., within 4 hours, or 2 hours, or 1 hour).

If the enzyme is added to the mixture too early, e.g., with the secondary additives or resin, the activity of the enzyme may decrease. Without intending to be bound by any particular theory, it is believed that boiling of the mixture with the enzyme leads to the enzyme denaturing and storing in solution for extended periods of time also leads to a reduction in enzyme activity.

In one class of embodiments, high enzyme activity is maintained in the water-soluble films according to the present disclosure by drying the films quickly under moderate to mild conditions. As used herein, drying quickly refers to a drying time of less than 24 hours, optionally less than 12 hours, optionally less than 8 hours, optionally less than 2 hours, optionally less than 1 hour, optionally less than 45 minutes, optionally less than 30 minutes, optionally less than 20 minutes, optionally less than 10 minutes, for example in a range of about 6 minutes to about 10 minutes, or 8 minutes. As used herein, moderate to mild conditions refer to drying temperatures of less than 170° F. (77° C.), optionally in a range of about 150° F. to about 170° F. (about 66° C. to about 77° C.), e.g., 165° F. (74° C.). As the drying temperature increases, the enzymes tend to denature faster, whereas as the drying temperature decreases, the drying time increases, thus exposing the enzymes to solution for an extended period of time.

The film is useful for creating a packet to contain a composition, for example laundry or dishwashing compositions, thereby forming a pouch. The film described herein can also be used to make a packet with two or more compartments made of the same film or in combination with films of other polymeric materials. Additional films can, for example, be obtained by casting, blow-molding, extrusion or blown extrusion of the same or a different polymeric material, as known in the art. In one type of embodiment, the polymers, copolymers or derivatives thereof suitable for use as the additional film are selected from polyvinyl alcohols, polyvinyl pyrrolidone, polyalkylene oxides, polyacrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthan, and carrageenans. For example, polymers can be selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and combinations thereof, or selected from polyvinyl alcohols, polyvinyl alcohol copolymers and hydroxypropyl methyl cellulose (HPMC), and combinations thereof.

The pouches and/or packets of the present disclosure comprise at least one sealed compartment. Thus the pouches may comprise a single compartment or multiple compartments. The pouches may have regions with and without enzymes. In embodiments including multiple compartments, each compartment may contain identical and/or different compositions. In turn, the compositions may take any suitable form including, but not limited to liquid, solid and combinations thereof (e.g., a solid suspended in a liquid). In some embodiments, the pouches comprises a first, second and third compartment, each of which respectively contains a different first, second and third composition. In some embodiments, the compositions may be visually distinct as described in EP 2258820.

The compartments of multi-compartment pouches and/or packets may be of the same or different size(s) and/or volume(s). The compartments of the present multi-compartment pouches can be separate or conjoined in any suitable manner. In some embodiments, the second and/or third and/or subsequent compartments are superimposed on the first compartment. In one embodiment, the third compartment may be superimposed on the second compartment, which is in turn superimposed on the first compartment in a sandwich configuration. Alternatively the second and third compartments may be superimposed on the first compartment. However it is also equally envisaged that the first, second and optionally third and subsequent compartments may be attached to one another in a side by side relationship. The compartments may be packed in a string, each compartment being individually separable by a perforation line. Hence each compartment may be individually torn-off from the remainder of the string by the end-user.

In some embodiments, multi-compartment pouches and/or packets include three compartments consisting of a large first compartment and two smaller compartments. The second and third smaller compartments are superimposed on the first larger compartment. The size and geometry of the compartments are chosen such that this arrangement is achievable. The geometry of the compartments may be the same or different. In some embodiments the second and optionally third compartment each has a different geometry and shape as compared to the first compartment. In these embodiments, the second and optionally third compartments are arranged in a design on the first compartment. The design may be decorative, educative, or illustrative, for example to illustrate a concept or instruction, and/or used to indicate origin of the product. In some embodiments, the first compartment is the largest compartment having two large faces sealed around the perimeter, and the second compartment is smaller covering less than about 75%, or less than about 50% of the surface area of one face of the first compartment. In embodiments in which there is a third compartment, the aforementioned structure may be the same but the second and third compartments cover less than about 60%, or less than about 50%, or less than about 45% of the surface area of one face of the first compartment.

The pouches and/or packets of the present disclosure may comprise one or more different films. For example, in single compartment embodiments, the packet may be made from one wall that is folded onto itself and sealed at the edges, or alternatively, two walls that are sealed together at the edges. In multiple compartment embodiments, the packet may be made from one or more films such that any given packet compartment may comprise walls made from a single film or multiple films having differing compositions. In one embodiment, a multi-compartment pouch comprises at least three walls: an outer upper wall; an outer lower wall; and a partitioning wall. The outer upper wall and the outer lower wall are generally opposing and form the exterior of the pouch. The partitioning wall is interior to the pouch and is secured to the generally opposing outer walls along a seal line. The partitioning wall separates the interior of the multi-compartment pouch into at least a first compartment and a second compartment. In one class of embodiments, the partitioning wall may be the only enzyme containing film thereby minimizing the exposure of the consumer to the enzymes.

Pouches and packets may be made using any suitable equipment and method. For example, single compartment pouches may be made using vertical form filling, horizontal form filling, or rotary drum filling techniques commonly known in the art. Such processes may be either continuous or intermittent. The film may be dampened, and/or heated to increase the malleability thereof. The method may also involve the use of a vacuum to draw the film into a suitable mold. The vacuum drawing the film into the mold can be applied for about 0.2 to about 5 seconds, or about 0.3 to about 3, or about 0.5 to about 1.5 seconds, once the film is on the horizontal portion of the surface. This vacuum can be such that it provides an under-pressure in a range of 10 mbar to 1000 mbar, or in a range of 100 mbar to 600 mbar, for example.

The molds, in which packets may be made, can have any shape, length, width and depth, depending on the required dimensions of the pouches. The molds may also vary in size and shape from one to another, if desirable. For example, the volume of the final pouches may be about 5 ml to about 300 ml, or about 10 to 150 ml, or about 20 to about 100 ml, and that the mold sizes are adjusted accordingly.

In one embodiment, the packet includes a first and a second sealed compartment. The second compartment is in a generally superposed relationship with the first sealed compartment such that the second sealed compartment and the first sealed compartment share a partitioning wall interior to the pouch.

In one embodiment, the packet including a first and a second compartment further includes a third sealed compartment. The third sealed compartment is in a generally superposed relationship with the first sealed compartment such that the third sealed compartment and the first sealed compartment share a partitioning wall interior to the pouch.

In various embodiments, the first composition and the second composition are selected from one of the following combinations: liquid, liquid; liquid, powder; powder, powder; and powder, liquid.

In various embodiments, the first, second and third compositions are selected from one of the following combinations: solid, liquid, liquid and liquid, liquid, liquid.

In one embodiment, the single compartment or plurality of sealed compartments contains a composition. The plurality of compartments may each contain the same or a different composition. The composition is selected from a liquid, solid or combination thereof.

Heat can be applied to the film in the process commonly known as thermoforming. The heat may be applied using any suitable means. For example, the film may be heated directly by passing it under a heating element or through hot air, prior to feeding it onto a surface or once on a surface. Alternatively, it may be heated indirectly, for example by heating the surface or applying a hot item onto the film. The film can be heated using an infrared light. The film may be heated to a temperature of at least 50° C., for example about 50 to about 150° C., about 50 to about 120° C., about 60 to about 130° C., about 70 to about 120° C., or about 60 to about 90° C.

Alternatively, the film can be wetted by any suitable means, for example directly by spraying a wetting agent (including water, a solution of the film composition, a plasticizer for the film composition, or any combination of the foregoing) onto the film, prior to feeding it onto the surface or once on the surface, or indirectly by wetting the surface or by applying a wet item onto the film.

Once a film has been heated and/or wetted, it may be drawn into an appropriate mold, preferably using a vacuum. The film can be thermoformed with a draw ratio of at least about 1.5, for example, and optionally up to a draw ratio of 2, for example. The filling of the molded film can be accomplished by utilizing any suitable means. In some embodiments, the most preferred method will depend on the product form and required speed of filling. In some embodiments, the molded film is filled by in-line filling techniques.

The filled, open packets are then closed forming the pouches, using a second film, by any suitable method. This may be accomplished while in horizontal position and in continuous, constant motion. The closing may be accomplished by continuously feeding a second film, preferably water-soluble film, over and onto the open packets and then preferably sealing the first and second film together, typically in the area between the molds and thus between the packets.

Any suitable method of sealing the packet and/or the individual compartments thereof may be utilized. Non-limiting examples of such means include heat sealing, solvent welding, solvent or wet sealing, and combinations thereof. The water-soluble packet and/or the individual compartments thereof can be heat sealed at a temperature of at least 200° F. (93° C.), for example in a range of about 220° F. (about 105° C.) to about 290° F. (about 145° C.), or about 230° F. (about 110° C.) to about 280° F. (about 140° C.). Typically, only the area which is to form the seal is treated with heat or solvent. The heat or solvent can be applied by any method, typically on the closing material, and typically only on the areas which are to form the seal. If solvent or wet sealing or welding is used, it may be preferred that heat is also applied. Preferred wet or solvent sealing/welding methods include selectively applying solvent onto the area between the molds, or on the closing material, by for example, spraying or printing this onto these areas, and then applying pressure onto these areas, to form the seal. Sealing rolls and belts as described above (optionally also providing heat) can be used, for example.

The formed pouches may then be cut by a cutting device. Cutting can be accomplished using any known method. It may be preferred that the cutting is also done in continuous manner, and preferably with constant speed and preferably while in horizontal position. The cutting device can, for example, be a sharp item, or a hot item, or a laser, whereby in the latter cases, the hot item or laser 'burns' through the film/sealing area.

The different compartments of a multi-compartment pouches may be made together in a side-by-side style wherein the resulting, cojoined pouches may or may not be separated by cutting. Alternatively, the compartments can be made separately.

In some embodiments, pouches may be made according to a process including the steps of:
a) forming a first compartment (as described above);
b) forming a recess within some or all of the closed compartment formed in step (a), to generate a second molded compartment superposed above the first compartment;
c) filling and closing the second compartments by means of a third film;
d) sealing the first, second and third films; and
e) cutting the films to produce a multi-compartment pouch.

The recess formed in step (b) may be achieved by applying a vacuum to the compartment prepared in step (a).

In some embodiments, second, and/or third compartment (s) can be made in a separate step and then combined with the first compartment as described in EP 2088187 or WO 2009/152031.

In other embodiments, pouches may be made according to a process including the steps of:
a) forming a first compartment, optionally using heat and/or vacuum, using a first film on a first forming machine;
b) filling the first compartment with a first composition;
c) on a second forming machine, deforming a second film, optionally using heat and vacuum, to make a second and optionally third molded compartment;
d) filling the second and optionally third compartments;
e) sealing the second and optionally third compartment using a third film;
f) placing the sealed second and optionally third compartments onto the first compartment;
g) sealing the first, second and optionally third compartments; and
h) cutting the films to produce a multi-compartment pouch.

The first and second forming machines may be selected based on their suitability to perform the above process. In some embodiments, the first forming machine is preferably a horizontal forming machine, and the second forming machine is preferably a rotary drum forming machine, preferably located above the first forming machine.

It should be understood that by the use of appropriate feed stations, it may be possible to manufacture multi-compartment pouches incorporating a number of different or distinctive compositions and/or different or distinctive liquid, gel or paste compositions.

Detergent Composition

The lipase containing water-soluble film of the invention may be used to form a compartment comprising a detergent composition, and thus encapsulating the detergent composition.

The detergent composition may be a solid or a liquid detergent composition. Preferably, the detergent composition is a liquid detergent composition having a physical form, which is not solid (or gas). It may be a pourable liquid, a pourable gel or a non-pourable gel. It may be either isotropic or structured, preferably isotropic. It may be a formulation useful for washing in automatic washing machines or for hand washing.

Liquids, including without limitation, alkanols, amines, diols, ethers and polyols may be included in a liquid detergent. A liquid detergent may contain from 0-30% organic solvent. A liquid detergent may even be non-aqueous, or substantially non-aqueous, wherein the water content is below 15%, preferably below 10%, more preferably below 6%, more preferably below 4%, more preferably below 2%, and most preferably below 1%.

Detergent ingredients can be separated physically from each other by compartments in water dissolvable pouches. Thereby negative storage interaction between components can be avoided. Different dissolution profiles of each of the compartments can also give rise to delayed dissolution of selected components in the wash solution.

The detergent composition may take the form of a unit dose product. A unit dose product is the packaging of a single dose in a non-reusable container. It is increasingly used in detergents for laundry and dish wash. A detergent unit dose product is the packaging (e.g., in a pouch made from a water soluble film) of the amount of detergent used for a single wash.

Pouches can be of any form, shape and material which is suitable for holding the composition, e.g., without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be a blend compositions comprising hydrolytically degradable and water soluble polymer blends such as polyactide and polyvinyl alcohol plus plasticizers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids (see e.g., US 2009/0011970).

The choice of detergent components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

The choice of additional components is within the skill of the artisan and includes conventional ingredients, including the exemplary non-limiting components set forth below.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 0.1% to about 10% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 0.1% to about 20% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 0.1% to about 10% by weight of a zwitterionic surfactant. Non-limiting examples of zwitterionic surfactants include betaine, alkyldimethylbetaine, sulfobetaine, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see for example review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope.

Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg ions. Any builder and/or co-builder known in the art for use in laundry detergents may be utilized. Non-limiting examples of builders include citrates, zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2"-nitrilotriethanol), and carboxymethyl inulin (CMI), and combinations thereof.

The detergent composition may also contain 0-50% by weight, such as about 5% to about 30%, of a detergent co-builder, or a mixture thereof. The detergent composition may include a co-builder alone, or in combination with a builder, for example a citrate builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N, N-diacetic acid (SEDA), isoserine-N, N-diacetic acid (ISDA), phenylalanine-N, N-diacetic acid (PHDA), anthranilic acid-N, N-diacetic acid (ANDA), sulfanilic acid-N, N-diacetic acid (SLDA), taurine-N, N-diacetic acid (TUDA) and sulfomethyl-N, N-diacetic acid (SMDA), N-(2-hydroxyethyl)-ethylidenediamine-N, N, N'-triacetate (HEDTA), diethanolglycine (DEG), diethylenetriamine penta (methylenephosphonic acid) (DTPMP), aminotris (methylenephosphonic acid) (ATMP), and combinations and salts thereof. Further exemplary builders and/or co-builders are described in, e.g., WO 09/102854, U.S. Pat. No. 5,977,053.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575 and U.S. Pat. No. 5,955,415. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257 and WO 2007/087243.

(Additional) Enzymes

Enzyme(s) which may be comprised in the detergent composition include one or more enzymes such as protease, lipase, cutinase, amylase, carbohydrase, cellulase, pectinase, mannanase, arabinase, galactanase, xylanase, DNAse, perhydrolase, oxidase, e.g., laccase, and/or peroxidase.

A typical combination of enzymes comprises, e.g., a protease and lipase in conjunction with amylase. When present in a composition, the aforementioned additional enzymes may be present at levels from 0.00001 to 2 wt %, from 0.0001 to 1 wt % or from 0.001 to 0.5 wt % enzyme protein by weight of the composition.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/01544.

Other cellulases are endo-beta-1,4-glucanase enzyme having a sequence of at least 97% identity to the amino acid sequence of position 1 to position 773 of SEQ ID NO:2 of WO 02/099091 or a family 44 xyloglucanase, which a xyloglucanase enzyme having a sequence of at least 60% identity to positions 40-559 of SEQ ID NO: 2 of WO 01/062903.

Commercially available cellulases include Celluzyme™, and Carezyme™ (Novozymes NS) Carezyme Premium™ (Novozymes NS), Celluclean™ (Novozymes NS), Celluclean Classic™ (Novozymes NS), Cellusoft™ (Novozymes NS), Whitezyme™ (Novozymes NS), Clazinase™, and Puradax HA™ (Genencor International Inc.), and KAC-500(B)™ (Kao Corporation).

Lyases: The lyase may be a pectate lyase derived from *Bacillus*, particularly *B. licherniformis* or *B. agaradhaerens*, or a variant derived of any of these, e.g. as described in U.S. Pat. No. 6,124,127, WO 99/27083, WO 99/27084, WO 02/006442, WO 02/092741, WO 03/095638, Commercially available pectate lyases are XPect™; Pectawash™ and Pectaway™ (Novozymes NS).

Mannanases: Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway™ (Novozymes NS).

Proteases: Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the 51 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., 1991, *Protein Engng.* 4: 719-737 and Siezen et al., 1997, *Protein Science* 6: 501-523.

Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO 2009/021867, and subtilisin lentus, subtilisin Novo, subtilisin Carlsberg, *Bacillus licheniformis*, subtilisin BPN', subtilisin 309, subtilisin 147 and subtilisin 168 described in WO 89/06279 and protease PD138 described in (WO 93/18140). Other useful proteases may be those described in WO 92/175177, WO 01/16285, WO 02/026024 and WO 02/016547. Examples of trypsin-like proteases are trypsin (e.g. of porcine or bovine origin) and the *Fusarium* protease described in WO 89/06270, WO 94/25583 and WO 2005/040372, and the chymotrypsin proteases derived from *Cellumonas* described in WO 2005/052161 and WO 2005/052146.

A further preferred protease is the alkaline protease from *Bacillus lentus* DSM 5483, as described for example in WO 95/23221, and variants thereof which are described in WO 92/21760, WO 95/23221, EP 1921147 and EP 1921148.

Examples of metalloproteases are the neutral metalloprotease as described in WO 2007/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO2004/03186, WO2004/041979, WO2007/006305, WO2011/036263, WO2011/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V41, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V2051, L217D, N218D, M222S, A232V, K235L, Q236H, Q245R, N252K, T274A (using BPN' numbering).

Suitable commercially available protease enzymes include those sold under the trade names Alcalase™, Duralase™, Durazym™, Relase™, Relase™ Ultra, Savinase™, Savinase™ Ultra, Primase™, Polarzyme™, Kannase™, Liquanase™, Liquanase™ Ultra, Ovozyme™ Coronase™, Coronase™ Ultra, Neutrase™, Everlase™ and Esperase™ (Novozymes NS), those sold under the tradename Maxatase™, Maxacal™, Maxapem™, Purafect™, Purafect Prime™, Preferenz™, Purafect MA™, Purafect Ox™, Purafect OxP™, Puramax™ Properase™, Effectenz™, FN2™, FN3™, FN4™, Excellase™, Opticlean™ and Optimase™ (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases: Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, LiPeX™, Lipolex™ and Lipoclean™ (Novozymes NS), Lumafast™ (originally from Genencor) and Lipomax™ (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach™ from Huntsman Textile Effects Pte Ltd (WO10/100028).

Amylases: Suitable amylases include alpha-amylases and/or glucoamylases and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:
E187P+I203Y+G476K
E187P+I203Y+R458N+T459S+D460T+G476K
wherein the variants optionally further comprises a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:
N21D+D97N+V128I
wherein the variants optionally further comprises a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X™ and BAN™ (from Novozymes NS), and Rapidase™, Purastar™/Effectenz™, Powerase™, Preferenz S1000™, Preferenz S100™ and Preferenz S110™ (from Genencor International Inc./DuPont).

Deoxyribonuclease (DNase): Suitable deoxyribonucleases (DNases) are any enzyme that catalyzes the hydrolytic cleavage of phosphodiester linkages in the DNA backbone, thus degrading DNA. According to the invention, a DNase which is obtainable from a bacterium is preferred; in particular a DNase which is obtainable from a *Bacillus* is preferred; in particular a DNase which is obtainable from *Bacillus subtilis* or *Bacillus licheniformis* is preferred. Examples of such DNases are described in patent application WO 2011/098579 or in PCT/EP2013/075922.

Perhydrolases: Suitable perhydrolases are capable of catalyzing a perhydrolysis reaction that results in the production of a peracid from a carboxylic acid ester (acyl) substrate in the presence of a source of peroxygen (e.g., hydrogen peroxide). While many enzymes perform this reaction at low levels, perhydrolases exhibit a high perhydrolysis:hydrolysis ratio, often greater than 1. Suitable perhydrolases may be of plant, bacterial or fungal origin. Chemically modified or protein engineered mutants are included.

Examples of useful perhydrolases include naturally occurring *Mycobacterium* perhydrolase enzymes, or variants thereof. An exemplary enzyme is derived from *Mycobacterium smegmatis*. Such enzyme, its enzymatic properties, its structure, and variants thereof, are described in WO 2005/056782, WO 2008/063400, US 2008/145353, and US2007167344.

Peroxidases/Oxidases: Suitable peroxidases are comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago*, *Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In an preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be derived from plants, bacteria or fungi (including filamentous fungi and yeasts).

Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885).

Suitable examples from bacteria include a laccase derivable from a strain of *Bacillus*. A laccase derived from *Coprinopsis* or *Myceliophthora* is preferred; in particular a laccase derived from *Coprinopsis cinerea*, as disclosed in WO 97/08325; or from *Myceliophthora thermophila*, as disclosed in WO 95/33836.

If small amounts of lipase leak from the water-soluble film of the invention, the lipase(s) comprised in the water-soluble film may reduce the stability of certain detergent components (e.g., polymers with ester bonds, hydrogenated castor oil, perfume, methyl ester sulfonate surfactants). Therefore, it may be an advantage to add a protease to the detergent composition, which is then used as a scavenger to degrade the leaked lipase, and thus avoid degradation of sensitive detergent components.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a liquid, slurry, or even a granulate, etc.

Enzyme Stabilizers

Enzymes for use in compositions can be stabilized by various techniques. The enzymes employed herein can be stabilized by the presence of water-soluble sources of calcium and/or magnesium ions. Examples of conventional stabilizing agents are, e.g. a polyol such as propylene glycol or glycerol, a sugar or sugar alcohol, a peptide aldehyde, lactic acid, boric acid, or a boric acid derivative, e.g. an aromatic borate ester, or a phenyl boronic acid derivative such as 4-formylphenyl boronic acid, and the composition may be formulated as described in, for example, WO92/19709 and WO92/19708 In case of aqueous compositions comprising protease, a reversible protease inhibitor, such as a boron compound including borate, 4-formyl phenylboronic acid, phenylboronic acid and derivatives thereof, or compounds such as calcium formate, sodium formate and 1,2-propane diol can be added to further improve stability. The peptide aldehyde may be of the formula $B_2-B_1-B_0-R$ wherein: R is hydrogen, $CH_3$, $CX_3$, $CHX_2$, or $CH_2X$, wherein X is a halogen atom; $B_0$ is a phenylalanine residue with an OH substituent at the p-position and/or at the m-position; $B_1$ is a single amino acid residue; and $B_2$ consists of one or more amino acid residues, optionally comprising an N-terminal protection group. Preferred peptide aldehydes include but are not limited to: Z-RAY-H, Ac-GAY-H, Z-GAY-H, Z-GAL-H, Z-GAF-H, Z-GAV-H, Z-RVY-H, Z-LVY-H, Ac-LGAY-H, Ac-FGAY-H, Ac-YGAY-H, Ac-FGVY-H or Ac-WLVY-H, where Z is benzyloxycarbonyl and Ac is acetyl.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants—The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents—The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent—The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxyethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil release polymers—The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents—The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers are structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Bleaching Systems

The detergent compositions of the present invention may also include a bleaching system. Due to the incompatibility of the components there are still only few examples of liquid detergents combining bleach and enzymes (e.g., U.S. Pat. No. 5,275,753 or WO 99/00478). The lipase containing water-soluble film described in this invention can be used to separate bleach from lipase in liquid detergents. The detergent may contain 0-50% of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetylethylene diamine (TAED), sodium 4-[(3,5,5-trimethylhexanoyl)oxy]benzene sulfonate (ISONOBS), diperoxy dodecanoic acid, 4-(dodecanoyloxy)benzenesulfonate (LOBS), 4-(decanoyloxy)benzenesulfonate, 4-(decanoyloxy)benzoate (DOBS), 4-(nonanoyloxy)-benzenesulfonate (NOBS), and/or those disclosed in WO 98/17767. A particular family of bleach activators of interest was disclosed in EP624154 and particulary preferred in that family is acetyl triethyl citrate (ATC). ATC or a short chain triglyceride like triacetin has the advantage that it is environmental friendly as it eventually degrades into citric acid and alcohol. Furthermore acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

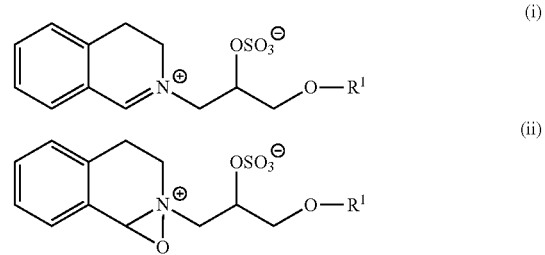

and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO 2007/087258, WO 2007/087244, WO 2007/087259 and WO 2007/087242. Suitable photobleaches may for example be sulfonated zinc phthalocyanine.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

The detergent pouch of the present invention is configured as single or multi compartments (see e.g., WO 2009/098660 or WO 2010/141301). It can be of any form, shape and material which is suitable for holding the detergent composition, e.g., without allowing release of the composition from the pouch prior to water contact. The pouch is made from water-soluble film which encloses the inner volume (detergent composition). Said inner volume can be divided into compartments of the pouch. The water-soluble film is described above under "Water-soluble film". The pouch can comprise a solid laundry cleaning (detergent) composition or selected components thereof, and/or a liquid cleaning composition or selected components thereof, separated by the water-soluble film. The pouch may include compartments having any combination of solids and liquids, both in one or more separate compartments, and in shared compartments containing both solid and liquid ingredients. The pouch may include regions or compartments formed by different water-soluble films, which can be with or without enzymes. Accordingly, detergent ingredients can be separated physically from each other in different compartments, or in different layers of a tablet if the detergent is in that physical form. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Compositions, Methods and Uses

In a first aspect, the present invention provides a water-soluble film comprising a variant of a parent lipase, which variant has lipase activity, has at least 60% but less than 100% sequence identity with SEQ ID NO: 2, and comprises substitutions at positions corresponding to T231R+N233R and at least one or more (e.g., several) of D96E, D111A, D254S, G163K, P256T, G91T and G38A of SEQ ID NO: 2.

In an embodiment, the variant further comprises substitutions at positions corresponding to D27R and/or N33Q of SEQ ID NO: 2.

In an embodiment, the variant comprises substitutions of SEQ ID NO: 2 selected from the group consisting of:
a) D96E+T231R+N233R;
b) N33Q+D96E+T231R+N233R;
c) N33Q+D111A+T231R+N233R;
d) N33Q+T231R+N233R+P256T;
e) N33Q+G38A+G91T+G163K+T231R+N233R+D254S;
f) N33Q+G38A+G91T+D96E+D111A+G163K+T231R+N233R+D254S+P256T;
g) D27R+N33Q+G38A+D96E+D111A+G163K+T231R+N233R+D254S+P256T;
h) D27R+N33Q+G38A+G91T+D96E+D111A+G163K+T231R+N233R+P256T;
i) D27R+N33Q+G38A+G91T+D96E+D111A+G163K+T231R+N233R+D254S;
j) D27R+G38A+G91T+D96E+D111A+G163K+T231R+N233R+D254S+P256T;
k) D96E+T231R+N233R+D254S;
l) T231R+N233R+D254S+P256T;
m) G163K+T231R+N233R+D254S;
n) D27R+N33Q+G38A+G91T+D96E+G163K+T231R+N233R+D254S+P256T;
o) D27R+G91T+D96E+D111A+G163K+T231R+N233R+D254S+P256T;
p) D96E+G163K+T231R+N233R+D254S;
q) D27R+G163K+T231R+N233R+D254S;
r) D27R+G38A+G91T+D96E+D111A+G163K+T231R+N233R+D254S;
s) D27R+G38A+G91T+D96E+G163K+T231R+N233R+D254S+P256T;
t) D27R+G38A+D96E+D111A+G163K+T231R+N233R+D254S+P256T;
u) D27R+D96E+G163K+T231R+N233R+D254S;
v) D27R+D96E+D111A+G163K+T231R+N233R+D254S+P256T;
w) D27R+G38A+D96E+G163K+T231R+N233R+D254S+P256T;
x) D111A+G163K+T231R+N233R+D254S+P256T;
y) D111A+T231R+N233R;
z) D111A+T231R+N233R+D254S+P256T;
aa) D27R+D96E+D111A+G163K+T231R+N233R;
bb) D27R+D96E+D111A+T231R+N233R;
cc) D27R+G38A+D96E+D111A+G163K+T231R+N233R+D254S+P256T;
dd) D27R+N33Q+G38A+D96E+D111A+T231R+N233R+D254S+P256T;
ee) D27R+G38A+D96E+D111A+G163K+E210Q+T231R+N233R+D254S+P256T;
ff) D27R+T231R+N233R+D254S+P256T;
gg) D96E+D111A+G163K+T231R+N233R;
hh) D96E+D111A+G163K+T231R+N233R+D254S+P256T;
ii) D96E+D111A+G163K+T231R+N233R+P256T;
jj) D96E+D111A+T231R+N233R;
kk) D96E+D111A+T231R+N233R+D254S;
ll) D96E+D111A+T231R+N233R+D254S+P256T;
mm) D96E+D111A+T231R+N233R+P256T;
nn) D96E+G163K+T231R+N233R+D254S+P256T;
oo) D96E+T231R+N233R+D254S+P256T;
pp) D96E+T231R+N233R+P256T;
qq) G38A+D96E+D111A+T231R+N233R;
rr) G91T+D96E+D111A+G163K+T231R+N233R+D254S+P256T;
ss) G91T+D96E+D111A+T231R+N233R;
tt) G91T+D96E+T231R+N233R;
uu) G91T+T231R+N233R+D254S+P256T;
vv) N33Q+D96E+D111A+G163K+T231R+N233R+D254S+P256T;
ww) T231R+N233R+D254S+P256T; and
xx) T231R+N233R+P256T.

In an embodiment, the variant has increased stability when compared to the parent lipase, under the same conditions. Preferably, the stability is stability under storage conditions, stability in the presence of surfactants; stability in the presence of protease, stability in the presence of protease and surfactants; stability in the presence of detergent components; chemical stability, oxidation stability, pH stability, and/or thermostability.

In an embodiment, the variant is selected from the group consisting of:
a) a polypeptide having at least 60%, at least 65%, at least 70%, at least 75%, at least 80%, at least 85%, at least 90%, at least 95% identity, at least 96%, at least 97%, at least 98%, or at least 99%, but less than 100%, sequence identity to SEQ ID NO: 2;
b) a polypeptide encoded by a polynucleotide that hybridizes under low stringency conditions, medium stringency conditions, medium-high stringency conditions, high stringency conditions, or very high stringency conditions with (i) the polypeptide coding sequence of SEQ ID NO: 1 or (ii) the full-length complement of (i);
c) a polypeptide encoded by a polynucleotide having at least 60%, at least 65%, at least 70%, at least 75%, at least 80%, at least 85%, at least 90%, at least 95%, at least 96%, at least 97%, at least 98%, at least 99%, but less than 100% sequence identity to SEQ ID NO: 1; and
d) a fragment of the polypeptide of SEQ ID NO: 2.

In an embodiment, the variant is in a solid particulate form, as lipase particles. Preferably, the size of the lipase particles is from 0.5 μm to 100 μm. Preferably, the lipase particles are enzyme crystals. Preferably, the lipase particles contain at least 1% w/w lipase protein.

In an embodiment, the water-soluble film comprises an additional (detergent) enzyme selected from the group consisting of protease, lipase, cutinase, amylase, carbohydrase, cellulase, pectinase, mannanase, arabinase, galactanase, xylanase, DNAse, perhydrolase, and oxidase.

In an embodiment, the water-soluble film comprises from 35% to 90% of PVOH which has a degree of hydrolysis of from 75% to 99%.

In an embodiment, the water-soluble film comprises from 10% to 50% of polyols.

In an embodiment, the thickness of the water-soluble film is from 10 μm to 500 μm, preferably from 10 μm to 300 μm, more preferably from 20 μm to 200 μm, and most preferably from 25 μm to 150 μm.

In an embodiment, the water-soluble film covers an area of at least 1 cm², preferably 2 cm², more preferably 5 cm², and most preferably 10 cm².

The water-soluble film of the invention is useful for encapsulating a detergent composition. Accordingly, in another aspect, the invention provides a detergent pouch, comprising a compartment formed by the water-soluble film of the invention (as described above), and a detergent composition containing a surfactant and/or a detergent builder.

In an embodiment, the detergent composition is a laundry or dish wash detergent composition.

In an embodiment, the detergent composition is a liquid detergent composition.

In an embodiment, the liquid detergent composition is substantially non-aqueous.

In an embodiment, the detergent pouch comprises an additional enzyme selected from the group consisting of protease, lipase, cutinase, amylase, carbohydrase, cellulase, pectinase, mannanase, arabinase, galactanase, xylanase, DNAse, perhydrolase, and oxidase.

In yet another aspect, the invention provides a method for preparing the detergent pouch of the invention, comprising encapsulating a detergent composition with the water-soluble film of the invention.

The invention also provides for use of the methods and compositions above for improving lipase storage stability, and/or improving residual lipase activity (recovery of enzymatic activity) after preparing the water-soluble film described above.

The present invention is further described by the following examples which should not be construed as limiting the scope of the invention.

EXAMPLES

Chemicals used as buffers and substrates were commercial products of at least reagent grade.

Example 1

Improved Storage Stability of Lipase Containing Water-soluble Film

Two water-soluble films were prepared as described in WO2013/138288, Example 1 (without protease, amylase, and protease substrate) as follows:

Film A:
0.25% wt. of active lipase enzyme having the amino acid sequence of SEQ ID NO: 2 with the substitutions T231R+N233R (reference lipase). The amino acid sequence is also shown as SEQ ID NO: 3.

Film B:
0.25% wt. of active lipase enzyme having the amino acid sequence of SEQ ID NO: 2 with the substitutions D27R+G38A+D96E+D111A+G163K+T231R+N233R+D254S+P256T (lipase variant of the invention). The amino acid sequence is also shown as SEQ ID NO: 4.

One gram water-soluble film was immersed in 20 g of a unit dose detergent (the white liquid phase taken out from the largest chamber of Tide Pods, commercially bought in the United States in 2012) and subsequently stored in closed glasses at 22, 30 and 37° C. for up to 4 weeks. Films was taken out of the detergent and analyzed for lipase activity using standard lipase analysis (hydrolysis of p-nitrophenyl palmitate at 37° C., pH=8.0) and compared with the activity of samples stored at −18° C. (reference).

TABLE 1

Storage stability of lipase in water-soluble film.

| Storage temp | Time | Residual Lipase activity | |
|---|---|---|---|
| | | Film A | Film B |
| 30° C. | 2 weeks | 59% | 67% |
| | 4 weeks | 37% | 57% |
| 37° C. | 2 weeks | 14% | 55% |
| | 4 weeks | 0% | 47% |

The data in Table 1 show that Film B (with the lipase variant of the invention) has considerably higher residual lipase activity than Film A (with the reference lipase), especially at elevated temperature.

Example 2

Detergent Storage Stability of Lipase Containing Water-soluble Film

Films were prepared with film solutions as in Example 1 (but without addition of plasticizers) with addition of two lipase variants of the invention, and a reference lipase:

Lipase 1 has the amino acid sequence of SEQ ID NO: 2 with the substitutions T231R+N233R (reference lipase).
Lipase 2 has the amino acid sequence of SEQ ID NO: 2 with the substitutions D27R+G38A+D96E+D111A+G163K+T231R+N233R+I238C+A243T+T244Y+G246C+D254S+P256T.
Lipase 3 has the amino acid sequence of SEQ ID NO: 2 with the substitutions D27R+G38A+K46R+S54T+D96E+D111A+G163K+T231R+N233R+D254S+P256T.

Five ml of an approximately 8% solids film solution with lipase was added to a 50 mm diameter plastic Petri dish, and the solution was allowed to dry in the laboratory overnight. Subsequently the film was finally dried 3 hours at 50° C. The final film contained about 15 mg/g lipase protein. For each lipase, two glasses with about 0.2 g film were immersed in 10 g Tide Pods detergent (as in Example 1)—one glass was stored at 37° C. for 7 days, the other glass was stored at −18° C. (reference).

---

The invention claimed is:

1. A water-soluble film comprising a variant of a parent lipase, which variant has lipase activity, has at least 60% but less than 100% sequence identity with SEQ ID NO: 2, and comprises substitutions at positions corresponding to T231R+N233R and at least one or more of D96E, D111A, D254S, G163K, P256T, G91T and G38A of SEQ ID NO: 2.

2. The water-soluble film of claim 1, wherein the variant further comprises substitutions at positions corresponding to D27R and/or N33Q of SEQ ID NO: 2.

3. The water-soluble film of claim 1, wherein the variant comprises substitutions of SEQ ID NO: 2 selected from the group consisting of:
   a) D96E+T231R+N233R;
   b) N33Q+D96E+T231R+N233R;
   c) N33Q+D111A+T231R+N233R;
   d) N33Q+T231R+N233R+P256T;
   e) N33Q+G38A+G91T+G163K+T231R+N233R+D254S;
   f) N33Q+G38A+G91T+D96E+D111A+G163K+T231R+N233R+D254S+P256T;
   g) D27R+N33Q+G38A+D96E+D111A+G163K+T231R+N233R+D254S+P256T;
   h) D27R+N33Q+G38A+G91T+D96E+D111A+G163K+T231R+N233R+P256T;
   i) D27R+N33Q+G38A+G91T+D96E+D111A+G163K+T231R+N233R+D254S;
   j) D27R+G38A+G91T+D96E+D111A+G163K+T231R+N233R+D254S+P256T;
   k) D96E+T231R+N233R+D254S;
   l) T231R+N233R+D254S+P256T;
   m) G163K+T231R+N233R+D254S;
   n) D27R+N33Q+G38A+G91T+D96E+G163K+T231R+N233R+D254S+P256T;
   o) D27R+G91T+D96E+D111A+G163K+T231R+N233R+D254S+P256T;
   p) D96E+G163K+T231R+N233R+D254S;
   q) D27R+G163K+T231R+N233R+D254S;
   r) D27R+G38A+G91T+D96E+D111A+G163K+T231R+N233R+D254S;
   s) D27R+G38A+G91T+D96E+G163K+T231R+N233R+D254S+P256T;
   t) D27R+G38A+D96E+D111A+G163K+T231R+N233R+D254S+P256T;
   u) D27R+D96E+G163K+T231R+N233R+D254S;
   v) D27R+D96E+D111A+G163K+T231R+N233R+D254S+P256T;
   w) D27R+G38A+D96E+G163K+T231R+N233R+D254S+P256T;
   x) D111A+G163K+T231R+N233R+D254S+P256T;
   y) D111A+T231R+N233R;
   z) D111A+T231R+N233R+D254S+P256T;
   aa) D27R+D96E+D111A+G163K+T231R+N233R;
   bb) D27R+D96E+D111A+T231R+N233R;
   cc) D27R+G38A+D96E+D111A+G163K+T231R+N233R+D254S+P256T;
   dd) D27R+N33Q+G38A+D96E+D111A+T231R+N233R+D254S+P256T;
   ee) D27R+G38A+D96E+D111A+G163K+E210Q+T231R+N233R+D254S+P256T;
   ff) D27R+T231R+N233R+D254S+P256T;
   gg) D96E+D111A+G163K+T231R+N233R;

hh) D96E+D111A+G163K+T231R+N233R+D254S+P256T;
ii) D96E+D111A+G163K+T231R+N233R+P256T;
jj) D96E+D111A+G163K+T231R+N233R;
kk) D96E+D111A+T231R+N233R+D254S;
ll) D96E+D111A+T231R+N233R+D254S+P256T;
mm) D96E+D111A+T231R+N233R+P256T;
nn) D96E+G163K+T231R+N233R+D254S+P256T;
oo) D96E+T231R+N233R+D254S+P256T;
pp) D96E+T231R+N233R+P256T;
qq) G38A+D96E+D111A+T231R+N233R;
rr) G91T+D96E+D111A+G163K+T231R+N233R+D254S+P256T;
ss) G91T+D96E+D111A+T231R+N233R;
tt) G91T+D96E+T231R+N233R;
uu) G91T+T231R+N233R+D254S+P256T;
vv) N33Q+D96E+D111A+G163K+T231R+N233R+D254S+P256T;
ww) T231R+N233R+D254S+P256T; and
xx) T231R+N233R+P256T.

4. The water-soluble film of claim 1, wherein the variant in comparison with the parent lipase has increased stability.

5. The water-soluble film of claim 4, wherein the stability is stability under storage conditions, stability in the presence of surfactants; stability in the presence of protease, stability in the presence of protease and surfactants; stability in the presence of detergent components; chemical stability, oxidation stability, pH stability, and/or thermostability.

6. The water-soluble film of claim 1, wherein the variant is selected from the group consisting of:
   a) a polypeptide having at least 60%, but less than 100%, sequence identity to SEQ ID NO: 2;
   b) a polypeptide encoded by a polynucleotide that hybridizes under low stringency conditions, medium stringency conditions, medium-high stringency conditions, high stringency conditions, or very high stringency conditions with (i) the polypeptide coding sequence of SEQ ID NO: 1 or (ii) the full-length complement of (i);
   c) a polypeptide encoded by a polynucleotide having at least 60%, but less than 100% sequence identity to SEQ ID NO: 1; and
   d) a fragment of the polypeptide of SEQ ID NO: 2.

7. The water-soluble film of claim 1, wherein the variant is in a solid particulate form.

8. The water-soluble film of claim 1, wherein the water-soluble film comprises from 35% to 90% of polyvinyl alcohol (PVOH) which has a degree of hydrolysis of from 75% to 99%.

9. The water-soluble film of claim 1, wherein the water-soluble film comprises from 10% to 50% of polyols.

10. The water-soluble film of claim 1, wherein the thickness of the water-soluble film is from 10 µm to 500 µm.

11. A detergent pouch, comprising a compartment formed by the water-soluble film of claim 1, and a detergent composition containing a surfactant and/or a detergent builder.

12. The detergent pouch of claim 11, wherein the detergent composition is a laundry or dish wash detergent composition.

13. The detergent pouch of claim 11, wherein the detergent composition is a liquid detergent composition.

14. The detergent pouch of claim 11, wherein the liquid detergent composition is substantially non-aqueous.

15. The detergent pouch of claim 11, which comprises an additional enzyme selected from the group consisting of protease, lipase, cutinase, amylase, carbohydrase, cellulase, pectinase, mannanase, arabinase, galactanase, xylanase, DNAse, perhydrolase, and oxidase.

16. A method for preparing a detergent pouch, the method comprising encapsulating a detergent composition comprising a surfactant and/or a detergent builder with the water-soluble film of claim 1.

* * * * *

SEQUENCE LISTING

```
<160> NUMBER OF SEQ ID NOS: 4

<210> SEQ ID NO 1
<211> LENGTH: 807
<212> TYPE: DNA
<213> ORGANISM: Thermomyces lanuginosus
<220> FEATURE:
<221> NAME/KEY: CDS
<222> LOCATION: (1)..(807)
<220> FEATURE:
<221> NAME/KEY: mat_peptide
<222> LOCATION: (1)..()

<400> SEQUENCE: 1 gag gtc tcg cag gat ctg ttt aac cag ttc aat ctc ttt gca cag tat      48
Glu Val Ser Gln Asp Leu Phe Asn Gln Phe Asn Leu Phe Ala Gln Tyr
1               5                  10                  15 tct gca gcc gca tac tgc gga aaa aac aat gat gcc cca gct ggt aca      96
Ser Ala Ala Ala Tyr Cys Gly Lys Asn Asn Asp Ala Pro Ala Gly Thr
             20                  25                  30 aac att acg tgc acg gga aat gcc tgc ccc gag gta gag aag gcg gat     144
Asn Ile Thr Cys Thr Gly Asn Ala Cys Pro Glu Val Glu Lys Ala Asp
         35                  40                  45 gca acg ttt ctc tac tcg ttt gaa gac tct gga gtg ggc gat gtc acc     192
Ala Thr Phe Leu Tyr Ser Phe Glu Asp Ser Gly Val Gly Asp Val Thr
     50                  55                  60 ggc ttc ctt gct ctc gac aac acg aac aaa ttg atc gtc ctc tct ttc     240
Gly Phe Leu Ala Leu Asp Asn Thr Asn Lys Leu Ile Val Leu Ser Phe
65                  70                  75                  80 cgt ggc tct cgt tcc ata gag aac tgg atc ggg aat ctt aac ttc gac     288
Arg Gly Ser Arg Ser Ile Glu Asn Trp Ile Gly Asn Leu Asn Phe Asp
                 85                  90                  95 ttg aaa gaa ata aat gac att tgc tcc ggc tgc agg gga cat gac ggc     336
Leu Lys Glu Ile Asn Asp Ile Cys Ser Gly Cys Arg Gly His Asp Gly
            100                 105                 110 ttc act tcg tcc tgg agg tct gta gcc gat acg tta agg cag aag gtg     384
Phe Thr Ser Ser Trp Arg Ser Val Ala Asp Thr Leu Arg Gln Lys Val
        115                 120                 125 gag gat gct gtg agg gag cat ccc gac tat cgc gtg gtg ttt acc gga     432
Glu Asp Ala Val Arg Glu His Pro Asp Tyr Arg Val Val Phe Thr Gly
    130                 135                 140 cat agc ttg ggt ggt gca ttg gca act gtt gcc gga gca gac ctg cgt     480
His Ser Leu Gly Gly Ala Leu Ala Thr Val Ala Gly Ala Asp Leu Arg
145                 150                 155                 160 gga aat ggg tat gat atc gac gtg ttt tca tat ggc gcc ccc cga gtc     528
Gly Asn Gly Tyr Asp Ile Asp Val Phe Ser Tyr Gly Ala Pro Arg Val
                165                 170                 175 gga aac agg gct ttt gca gaa ttc ctg acc gta cag acc ggc gga aca     576
Gly Asn Arg Ala Phe Ala Glu Phe Leu Thr Val Gln Thr Gly Gly Thr
            180                 185                 190 ctc tac cgc att acc cac acc aat gat att gtc cct aga ctc ccg ccg     624
Leu Tyr Arg Ile Thr His Thr Asn Asp Ile Val Pro Arg Leu Pro Pro
        195                 200                 205
```

```
cgc gaa ttc ggt tac agc cat tct agc cca gag tac tgg atc aaa tct    672
Arg Glu Phe Gly Tyr Ser His Ser Ser Pro Glu Tyr Trp Ile Lys Ser
    210                 215                 220 gga acc ctt gtc ccc gtc acc cga aac gat atc gtg aag ata gaa ggc    720
Gly Thr Leu Val Pro Val Thr Arg Asn Asp Ile Val Lys Ile Glu Gly
225                 230                 235                 240 atc gat gcc acc ggc ggc aat aac cag cct aac att ccg gat atc cct    768
Ile Asp Ala Thr Gly Gly Asn Asn Gln Pro Asn Ile Pro Asp Ile Pro
                245                 250                 255 gcg cac cta tgg tac ttc ggg tta att ggg aca tgt ctt                807
Ala His Leu Trp Tyr Phe Gly Leu Ile Gly Thr Cys Leu
            260                 265
```

<210> SEQ ID NO 2
<211> LENGTH: 269
<212> TYPE: PRT
<213> ORGANISM: Thermomyces lanuginosus

<400> SEQUENCE: 2

```
Glu Val Ser Gln Asp Leu Phe Asn Gln Phe Asn Leu Phe Ala Gln Tyr
1               5                   10                  15

Ser Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
            35                  40                  45

Ala Thr Phe Leu Tyr Ser Phe Glu Asp Ser Gly Val Gly Asp Val Thr
        50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265
```

<210> SEQ ID NO 3
<211> LENGTH: 269

```
<212> TYPE: PRT
<213> ORGANISM: Artificial
<220> FEATURE:
<223> OTHER INFORMATION: Thermomyces lanuginosus lipase variant

<400> SEQUENCE: 3

Glu Val Ser Gln Asp Leu Phe Asn Gln Phe Asn Leu Phe Ala Gln Tyr
1               5                   10                  15

Ser Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
210                 215                 220

Gly Thr Leu Val Pro Val Arg Arg Arg Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265

<210> SEQ ID NO 4
<211> LENGTH: 269
<212> TYPE: PRT
<213> ORGANISM: Artificial
<220> FEATURE:
<223> OTHER INFORMATION: Thermomyces lanuginosus lipase variant

<400> SEQUENCE: 4

Glu Val Ser Gln Asp Leu Phe Asn Gln Phe Asn Leu Phe Ala Gln Tyr
1               5                   10                  15

Ser Ala Ala Tyr Cys Gly Lys Asn Asn Arg Ala Pro Ala Gly Thr
            20                  25                  30

Asn Ile Thr Cys Thr Ala Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60
```

```
Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Glu
                85                  90                  95

Leu Lys Glu Ile Asn Asp Ile Cys Ser Gly Cys Arg Gly His Ala Gly
            100                 105                 110

Phe Thr Ser Ser Trp Arg Ser Val Ala Asp Thr Leu Arg Gln Lys Val
            115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Lys Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
210                 215                 220

Gly Thr Leu Val Pro Val Arg Arg Arg Asp Ile Val Lys Ile Glu Gly
225                 230                 235                 240

Ile Asp Ala Thr Gly Gly Asn Asn Gln Pro Asn Ile Pro Ser Ile Thr
                245                 250                 255

Ala His Leu Trp Tyr Phe Gly Leu Ile Gly Thr Cys Leu
            260                 265
```